(12) United States Patent
Tsukahara et al.

(10) Patent No.: US 8,323,917 B2
(45) Date of Patent: Dec. 4, 2012

(54) METHOD OF SCREENING FOR COMPOUNDS THAT INHIBIT THE ENZYMATIC ACTIVITY OF GWT1 GENE PRODUCT

(75) Inventors: Kappei Tsukahara, Tsukuba (JP); Mamiko Tsuchiya, Ushiku (JP); Yoshifumi Jigami, Tsukuba (JP); Kenichi Nakayama, Tsukuba (JP); Mariko Umemura, Tsukuba (JP); Michiyo Okamoto, Tsukuba (JP)

(73) Assignees: National Institute of Advanced Industrial Science and Technology, Tokyo (JP); Eisai R&D Management Co., Ltd., Tokyo (JP)

( * ) Notice: Subject to any disclaimer, the term of this patent is extended or adjusted under 35 U.S.C. 154(b) by 1219 days.

(21) Appl. No.: 10/536,935

(22) PCT Filed: Nov. 21, 2003

(86) PCT No.: PCT/JP03/14909
§ 371 (c)(1),
(2), (4) Date: Feb. 15, 2006

(87) PCT Pub. No.: WO2004/048604
PCT Pub. Date: Jun. 10, 2004

(65) Prior Publication Data
US 2006/0240429 A1 Oct. 26, 2006

(30) Foreign Application Priority Data
Nov. 22, 2002 (JP) .................. 2002-339418

(51) Int. Cl.
*G01N 33/53* (2006.01)
*G01N 33/569* (2006.01)
*C12Q 1/68* (2006.01)
*C07H 21/04* (2006.01)
*C07K 1/00* (2006.01)
*C07K 14/00* (2006.01)
*C07K 17/00* (2006.01)

(52) U.S. Cl. ................... 435/7.31; 435/254.1; 435/6.13; 536/23.74; 530/350

(58) Field of Classification Search ............... 435/7.31, 435/254.1, 6.13; 536/23.74; 530/350
See application file for complete search history.

(56) References Cited

U.S. PATENT DOCUMENTS

| | | | |
|---|---|---|---|
| 6,747,137 B1 * | 6/2004 | Weinstock et al. ......... 536/23.1 |
| 2004/0038239 A1 | 2/2004 | Tsukahara et al. | |
| 2006/0172404 A1 | 8/2006 | Hata et al. | |
| 2006/0234349 A1 | 10/2006 | Tsukahara et al. | |
| 2008/0166765 A1 | 7/2008 | Tsukahara et al. | |
| 2008/0261272 A1 | 10/2008 | Tsukahara et al. | |
| 2009/0098636 A1 | 4/2009 | Tsukahara et al. | |
| 2009/0117586 A1 | 5/2009 | Tsukahara et al. | |
| 2009/0325228 A1 | 12/2009 | Tsukahara et al. | |

FOREIGN PATENT DOCUMENTS

| | | | |
|---|---|---|---|
| WO | WO/95/22614 | * | 8/1995 |
| WO | WO/02/04626 | * | 1/2002 |
| WO | WO 02/04626 A1 | | 1/2002 |
| WO | WO 03/058233 A1 | | 7/2003 |
| WO | WO 03/058233 A1 | * | 7/2003 |
| WO | WO 2004/048567 A2 | | 6/2004 |
| WO | WO 2004/048567 A3 | | 6/2004 |

OTHER PUBLICATIONS

Kinoshita, Taroh and Norimitsu Inoue; "Dissecting and manipulating the pathway for glycosylphophatidylinositol-anchor biosynthesis"; *Current Opinion in Chemical Biology* 4:632-638 (2000).

Hamada, K. et al.; "Screening for glycosylphosphatidylinositol (GPI)-dependent cell wall proteins in *Saccharomyces cerevisiae*"; *Mol. Gen. Genet.*; 1998; pp. 53-59; vol. 258.

Umemura, Mariko et al.; "*GWT1* Gene Is Required for Inositol Acylation of Glycosylphosphatidylinositol Anchors in Yeast"; *The Journal of Biological Chemistry*; Jun. 27, 2003; pp. 23639-23647; vol. 278, No. 26.

Murakami, et al., "PIG-W is Critical for Inositol Acylation but Not for Flipping of Glycosylphosphatidylinositol-Anchor," Molecular Biology of the Cell, vol. 14, Oct. 2003, 4285-4295.

Umemura et al., "GWT1 Gene is Required for Inositol Acylation of Glycosylphosphatidylinositol Anchors in Yeast," The Journal of Biological Chemistry, vol. 278, No. 26, Jun. 27, 2003, 23639-23647.

International Search report issued for International Application No. PCT/JP03/14909, dated Dec. 24, 2003.

Office Action issued for Chinese Patent Application No. 200380109116.9 dated Mar. 2, 2007.

Search Report issued for European Patent Application No. 03774148.5 dated Mar. 6, 2006.

Office Action issued for Japanese Patent Application No. JP2004-555006 dated Sep. 5, 2007.

* cited by examiner

*Primary Examiner* — Gary Nickol
*Assistant Examiner* — Nina Archie
(74) *Attorney, Agent, or Firm* — Kilpatrick Townsend & Stockton LLP

(57) ABSTRACT

The present invention enables screening for compounds that inhibit the transport of GPI-anchored proteins to fungal cell walls, using a simple assay for transacylation to GlcN-PI using membrane fraction expressing GWT1 protein. New antifungal agents can be created that inhibit the synthesis of fungal cell walls and also inhibit adhesion to host cells by inhibiting the transport of GPI-anchored proteins to fungal cell walls.

4 Claims, 4 Drawing Sheets

SEQUENCE LISTING

```
<160> NUMBER OF SEQ ID NOS: 18

<210> SEQ ID NO 1
<211> LENGTH: 1497
<212> TYPE: DNA
<213> ORGANISM: Saccharomyces cerevisiae
<220> FEATURE:
<221> NAME/KEY: CDS
<222> LOCATION: (1)..(1497)
<223> OTHER INFORMATION: GWT1

<400> SEQUENCE: 1 atg gca aca gta cat cag aag aat atg tcg act tta aaa cag aga aaa      48
Met Ala Thr Val His Gln Lys Asn Met Ser Thr Leu Lys Gln Arg Lys
  1               5                  10                  15 gag gac ttt gtg aca ggg ctc aat ggc ggt tct ata aca gaa att aac      96
Glu Asp Phe Val Thr Gly Leu Asn Gly Gly Ser Ile Thr Glu Ile Asn
             20                  25                  30 gca gtg aca tca att gct ttg gta act tac ata tca tgg aac tta ttg     144
Ala Val Thr Ser Ile Ala Leu Val Thr Tyr Ile Ser Trp Asn Leu Leu
         35                  40                  45 aaa aat tcc aac ctt atg cct cct ggc att tcc agc gtg caa tac ata     192
Lys Asn Ser Asn Leu Met Pro Pro Gly Ile Ser Ser Val Gln Tyr Ile
     50                  55                  60 att gat ttt gca ttg aac tgg gtt gct ttg ctt cta tct att act att     240
Ile Asp Phe Ala Leu Asn Trp Val Ala Leu Leu Leu Ser Ile Thr Ile
 65                  70                  75                  80 tat gct agt gaa cca tac ctt cta aac acg cta ata ctg tta cct tgt     288
Tyr Ala Ser Glu Pro Tyr Leu Leu Asn Thr Leu Ile Leu Leu Pro Cys
```

-continued

```
                    85                    90                      95
ttg ctc gca ttc ata tat gga aaa ttt act agc tcg agt aaa cct tct       336
Leu Leu Ala Phe Ile Tyr Gly Lys Phe Thr Ser Ser Ser Lys Pro Ser
                        100                 105                 110 aat cca ata tac aat aaa aaa aaa atg att aca cag cgg ttc caa cta       384
Asn Pro Ile Tyr Asn Lys Lys Lys Met Ile Thr Gln Arg Phe Gln Leu
                115                 120                 125 gaa aaa aag ccg tat att act gcg tat cgt ggt ggg atg ctt att ctg       432
Glu Lys Lys Pro Tyr Ile Thr Ala Tyr Arg Gly Gly Met Leu Ile Leu
        130                 135                 140 act gct att gcc atc ttg gct gta gat ttt cca att ttc cca agg agg       480
Thr Ala Ile Ala Ile Leu Ala Val Asp Phe Pro Ile Phe Pro Arg Arg
145                 150                 155                 160 ttt gcc aag gtg gaa act tgg ggg aca tcc ctg atg gat ctt ggt gta       528
Phe Ala Lys Val Glu Thr Trp Gly Thr Ser Leu Met Asp Leu Gly Val
                        165                 170                 175 gga tca ttc gtt ttc agt aac ggt att gtt tct tct agg gca ctg ttg       576
Gly Ser Phe Val Phe Ser Asn Gly Ile Val Ser Ser Arg Ala Leu Leu
                        180                 185                 190 aaa aac cta agc ttg aag agt aaa ccc agc ttc tta aaa aat gca ttt       624
Lys Asn Leu Ser Leu Lys Ser Lys Pro Ser Phe Leu Lys Asn Ala Phe
                195                 200                 205 aat gcc tta aaa tca gga gga act cta ttg ttc cta gga ttg ctg agg       672
Asn Ala Leu Lys Ser Gly Gly Thr Leu Leu Phe Leu Gly Leu Leu Arg
210                 215                 220 ttg ttt ttt gta aaa aat ttg gaa tat caa gaa cat gtc aca gaa tat       720
Leu Phe Phe Val Lys Asn Leu Glu Tyr Gln Glu His Val Thr Glu Tyr
225                 230                 235                 240 ggg gtt cat tgg aat ttt ttt atc acc cta tca ttg ttg cca ctt gta       768
Gly Val His Trp Asn Phe Phe Ile Thr Leu Ser Leu Leu Pro Leu Val
                        245                 250                 255 ttg acc ttt att gat ccc gtc aca aga atg gtt cca cgc tgc tca att       816
Leu Thr Phe Ile Asp Pro Val Thr Arg Met Val Pro Arg Cys Ser Ile
                260                 265                 270 gca ata ttc att tca tgc att tat gaa tgg cta ctt tta aag gac gat       864
Ala Ile Phe Ile Ser Cys Ile Tyr Glu Trp Leu Leu Leu Lys Asp Asp
                275                 280                 285 cgc act tta aac ttt tta att ttg gct gat aga aat tgt ttc ttc agt       912
Arg Thr Leu Asn Phe Leu Ile Leu Ala Asp Arg Asn Cys Phe Phe Ser
        290                 295                 300 gct aat aga gaa ggc atc ttc tca ttt cta ggt tat tgc tcg att ttt       960
Ala Asn Arg Glu Gly Ile Phe Ser Phe Leu Gly Tyr Cys Ser Ile Phe
305                 310                 315                 320 ctt tgg ggc caa aac acg gga ttt tac ttg ttg gga aat aaa cca act      1008
Leu Trp Gly Gln Asn Thr Gly Phe Tyr Leu Leu Gly Asn Lys Pro Thr
                        325                 330                 335 tta aac aat ctt tat aag cct tct acg caa gac gta gtt gca gca tca      1056
Leu Asn Asn Leu Tyr Lys Pro Ser Thr Gln Asp Val Val Ala Ala Ser
                340                 345                 350 aag aag tct tcg act tgg gac tat tgg act tca gta acc cca tta agt      1104
Lys Lys Ser Ser Thr Trp Asp Tyr Trp Thr Ser Val Thr Pro Leu Ser
            355                 360                 365 ggc ctc tgt ata tgg agt aca att ttt ctt gtt atc agc cag ttg gtt      1152
Gly Leu Cys Ile Trp Ser Thr Ile Phe Leu Val Ile Ser Gln Leu Val
        370                 375                 380 ttt caa tac cat cct tat agt gtt tca aga agg ttt gct aac tta cca      1200
Phe Gln Tyr His Pro Tyr Ser Val Ser Arg Arg Phe Ala Asn Leu Pro
385                 390                 395                 400 tat act ttg tgg gtc att act tat aat tta cta ttt ttg act ggg tac      1248
Tyr Thr Leu Trp Val Ile Thr Tyr Asn Leu Leu Phe Leu Thr Gly Tyr
```

```
                          405                 410                 415
tgc ttg act gac aaa att ttc ggt aat tct tcg gaa tat tat aaa gtt     1296
Cys Leu Thr Asp Lys Ile Phe Gly Asn Ser Ser Glu Tyr Tyr Lys Val
            420                 425                 430 gcc gaa tgc ttg gaa tca atc aac tcc aat ggg ttg ttt tta ttt ttg     1344
Ala Glu Cys Leu Glu Ser Ile Asn Ser Asn Gly Leu Phe Leu Phe Leu
                435                 440                 445 ttg gca aat gtc tct act ggt tta gtc aat atg tct atg gtc acg ata     1392
Leu Ala Asn Val Ser Thr Gly Leu Val Asn Met Ser Met Val Thr Ile
    450                 455                 460 gat tct tca ccc tta aaa tca ttc ctg gtt ttg ttg gca tac tgc tca     1440
Asp Ser Ser Pro Leu Lys Ser Phe Leu Val Leu Leu Ala Tyr Cys Ser
465                 470                 475                 480 ttc ata gct gtc ata tcg gtt ttc ttg tat aga aaa aga ata ttc att     1488
Phe Ile Ala Val Ile Ser Val Phe Leu Tyr Arg Lys Arg Ile Phe Ile
                485                 490                 495 aag cta taa                                                         1497
Lys Leu <210> SEQ ID NO 2
<211> LENGTH: 498
<212> TYPE: PRT
<213> ORGANISM: Saccharomyces cerevisiae
<220> FEATURE:
<223> OTHER INFORMATION: GWT1

<400> SEQUENCE: 2

Met Ala Thr Val His Gln Lys Asn Met Ser Thr Leu Lys Gln Arg Lys
  1               5                  10                  15

Glu Asp Phe Val Thr Gly Leu Asn Gly Gly Ser Ile Thr Glu Ile Asn
                 20                  25                  30

Ala Val Thr Ser Ile Ala Leu Val Thr Tyr Ile Ser Trp Asn Leu Leu
             35                  40                  45

Lys Asn Ser Asn Leu Met Pro Pro Gly Ile Ser Ser Val Gln Tyr Ile
         50                  55                  60

Ile Asp Phe Ala Leu Asn Trp Val Ala Leu Leu Leu Ser Ile Thr Ile
 65                  70                  75                  80

Tyr Ala Ser Glu Pro Tyr Leu Leu Asn Thr Leu Ile Leu Leu Pro Cys
                 85                  90                  95

Leu Leu Ala Phe Ile Tyr Gly Lys Phe Thr Ser Ser Ser Lys Pro Ser
            100                 105                 110

Asn Pro Ile Tyr Asn Lys Lys Lys Met Ile Thr Gln Arg Phe Gln Leu
        115                 120                 125

Glu Lys Lys Pro Tyr Ile Thr Ala Tyr Arg Gly Gly Met Leu Ile Leu
    130                 135                 140

Thr Ala Ile Ala Ile Leu Ala Val Asp Phe Pro Ile Phe Pro Arg Arg
145                 150                 155                 160

Phe Ala Lys Val Glu Thr Trp Gly Thr Ser Leu Met Asp Leu Gly Val
                165                 170                 175

Gly Ser Phe Val Phe Ser Asn Gly Ile Val Ser Ser Arg Ala Leu Leu
            180                 185                 190

Lys Asn Leu Ser Leu Lys Ser Lys Pro Ser Phe Leu Lys Asn Ala Phe
        195                 200                 205

Asn Ala Leu Lys Ser Gly Gly Thr Leu Leu Phe Leu Gly Leu Leu Arg
    210                 215                 220

Leu Phe Phe Val Lys Asn Leu Glu Tyr Gln Glu His Val Thr Glu Tyr
225                 230                 235                 240
```

-continued

```
Gly Val His Trp Asn Phe Phe Ile Thr Leu Ser Leu Leu Pro Leu Val
                245                 250                 255

Leu Thr Phe Ile Asp Pro Val Thr Arg Met Val Pro Arg Cys Ser Ile
            260                 265                 270

Ala Ile Phe Ile Ser Cys Ile Tyr Glu Trp Leu Leu Leu Lys Asp Asp
        275                 280                 285

Arg Thr Leu Asn Phe Leu Ile Leu Ala Asp Arg Asn Cys Phe Phe Ser
    290                 295                 300

Ala Asn Arg Glu Gly Ile Phe Ser Phe Leu Gly Tyr Cys Ser Ile Phe
305                 310                 315                 320

Leu Trp Gly Gln Asn Thr Gly Phe Tyr Leu Leu Gly Asn Lys Pro Thr
                325                 330                 335

Leu Asn Asn Leu Tyr Lys Pro Ser Thr Gln Asp Val Val Ala Ala Ser
            340                 345                 350

Lys Lys Ser Ser Thr Trp Asp Tyr Trp Thr Ser Val Thr Pro Leu Ser
        355                 360                 365

Gly Leu Cys Ile Trp Ser Thr Ile Phe Leu Val Ile Ser Gln Leu Val
    370                 375                 380

Phe Gln Tyr His Pro Tyr Ser Val Ser Arg Arg Phe Ala Asn Leu Pro
385                 390                 395                 400

Tyr Thr Leu Trp Val Ile Thr Tyr Asn Leu Leu Phe Leu Thr Gly Tyr
                405                 410                 415

Cys Leu Thr Asp Lys Ile Phe Gly Asn Ser Ser Glu Tyr Tyr Lys Val
            420                 425                 430

Ala Glu Cys Leu Glu Ser Ile Asn Ser Asn Gly Leu Phe Leu Phe Leu
        435                 440                 445

Leu Ala Asn Val Ser Thr Gly Leu Val Asn Met Ser Met Val Thr Ile
    450                 455                 460

Asp Ser Ser Pro Leu Lys Ser Phe Leu Val Leu Leu Ala Tyr Cys Ser
465                 470                 475                 480

Phe Ile Ala Val Ile Ser Val Phe Leu Tyr Arg Lys Arg Ile Phe Ile
                485                 490                 495

Lys Leu

<210> SEQ ID NO 3
<211> LENGTH: 1458
<212> TYPE: DNA
<213> ORGANISM: Candida albicans
<220> FEATURE:
<221> NAME/KEY: CDS
<222> LOCATION: (1)..(1458)
<223> OTHER INFORMATION: GWT1

<400> SEQUENCE: 3 atg tca tcg tct tta aaa caa ttg aaa gaa caa ttt gtc tca gat ttg      48
Met Ser Ser Ser Leu Lys Gln Leu Lys Glu Gln Phe Val Ser Asp Leu
 1               5                  10                  15 act ggt ggc aca att gaa gaa att tat gct gta acc agt ata gca tta      96
Thr Gly Gly Thr Ile Glu Glu Ile Tyr Ala Val Thr Ser Ile Ala Leu
            20                  25                  30 tca tct tat ttg tcc ttt aga ttg ttg aaa aag tct ctt ggt gat tta     144
Ser Ser Tyr Leu Ser Phe Arg Leu Leu Lys Lys Ser Leu Gly Asp Leu
        35                  40                  45 gct ttg att tac gac tac att ctt aat gtg ttg aca att cta gca tcc     192
Ala Leu Ile Tyr Asp Tyr Ile Leu Asn Val Leu Thr Ile Leu Ala Ser
    50                  55                  60 att act gtt tat agc aac agc cct tct tat ttg cat tat ttt att gtt     240
Ile Thr Val Tyr Ser Asn Ser Pro Ser Tyr Leu His Tyr Phe Ile Val
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     | 65  |     |     |     | 70  |     |     |     | 75  |     |     |     | 80  |     |
| att | cca | tca | tta | gtt | ata | tat | cta | gtg | aat | tac | cat | gtt | gag | aaa | cca | 288 |
| Ile | Pro | Ser | Leu | Val | Ile | Tyr | Leu | Val | Asn | Tyr | His | Val | Glu | Lys | Pro |     |
|     |     |     |     |     | 85  |     |     |     |     | 90  |     |     |     |     | 95  |     |
| tct | tca | ccc | cat | aga | caa | aat | gat | aca | aaa | gaa | gat | aaa | tcg | gac | gaa | 336 |
| Ser | Ser | Pro | His | Arg | Gln | Asn | Asp | Thr | Lys | Glu | Asp | Lys | Ser | Asp | Glu |     |
|     |     | 100 |     |     |     |     | 105 |     |     |     |     | 110 |     |     |     |     |
| cta | ttg | ccg | aga | aaa | caa | ttt | ata | aca | gcc | tat | cgt | tct | caa | atg | ttg | 384 |
| Leu | Leu | Pro | Arg | Lys | Gln | Phe | Ile | Thr | Ala | Tyr | Arg | Ser | Gln | Met | Leu |     |
|     | 115 |     |     |     |     | 120 |     |     |     |     | 125 |     |     |     |     |     |
| ata | att | act | aat | cta | gct | ata | tta | gct | gtt | gat | ttt | cct | att | ttc | cca | 432 |
| Ile | Ile | Thr | Asn | Leu | Ala | Ile | Leu | Ala | Val | Asp | Phe | Pro | Ile | Phe | Pro |     |
| 130 |     |     |     |     | 135 |     |     |     |     | 140 |     |     |     |     |     |     |
| aga | aga | ttt | gcc | aaa | gtg | gaa | aca | tgg | ggc | acg | tca | atg | atg | gat | tta | 480 |
| Arg | Arg | Phe | Ala | Lys | Val | Glu | Thr | Trp | Gly | Thr | Ser | Met | Met | Asp | Leu |     |
| 145 |     |     |     |     | 150 |     |     |     |     | 155 |     |     |     |     | 160 |     |
| gga | gtt | ggg | tcg | ttt | gtg | ttc | tcc | atg | ggg | ttg | gct | aat | tct | cga | caa | 528 |
| Gly | Val | Gly | Ser | Phe | Val | Phe | Ser | Met | Gly | Leu | Ala | Asn | Ser | Arg | Gln |     |
|     |     |     |     | 165 |     |     |     |     | 170 |     |     |     |     | 175 |     |     |
| ttg | atc | aag | aac | cac | acc | gac | aac | tac | aaa | ttt | agt | tgg | aag | agt | tat | 576 |
| Leu | Ile | Lys | Asn | His | Thr | Asp | Asn | Tyr | Lys | Phe | Ser | Trp | Lys | Ser | Tyr |     |
|     |     | 180 |     |     |     |     | 185 |     |     |     |     | 190 |     |     |     |     |
| ttg | aaa | aca | atc | aag | cag | aac | ttt | atc | aag | tca | gtg | cct | ata | ctt | gtt | 624 |
| Leu | Lys | Thr | Ile | Lys | Gln | Asn | Phe | Ile | Lys | Ser | Val | Pro | Ile | Leu | Val |     |
|     | 195 |     |     |     |     | 200 |     |     |     |     | 205 |     |     |     |     |     |
| tta | gga | gct | att | cgt | ttt | gtt | agt | gtt | aag | caa | ttg | gac | tat | cag | gaa | 672 |
| Leu | Gly | Ala | Ile | Arg | Phe | Val | Ser | Val | Lys | Gln | Leu | Asp | Tyr | Gln | Glu |     |
| 210 |     |     |     |     | 215 |     |     |     |     | 220 |     |     |     |     |     |     |
| cac | gaa | aca | gag | tat | gga | atc | cat | tgg | aat | ttt | ttc | ttc | aca | tta | ggg | 720 |
| His | Glu | Thr | Glu | Tyr | Gly | Ile | His | Trp | Asn | Phe | Phe | Phe | Thr | Leu | Gly |     |
| 225 |     |     |     |     | 230 |     |     |     |     | 235 |     |     |     |     | 240 |     |
| ttc | ttg | cca | att | gta | ttg | gga | ata | tta | gac | ccg | gtg | ttg | aat | ttg | gtt | 768 |
| Phe | Leu | Pro | Ile | Val | Leu | Gly | Ile | Leu | Asp | Pro | Val | Leu | Asn | Leu | Val |     |
|     |     |     |     | 245 |     |     |     |     | 250 |     |     |     |     | 255 |     |     |
| cca | cgc | ttc | ata | ata | gga | att | ggt | atc | tca | att | gct | tat | gag | gta | gcg | 816 |
| Pro | Arg | Phe | Ile | Ile | Gly | Ile | Gly | Ile | Ser | Ile | Ala | Tyr | Glu | Val | Ala |     |
|     |     || 260 |     |     |     |     | 265 |     |     |     |     | 270 |     |     |     |     |
| ttg | aat | aag | act | ggt | ttg | ttg | aag | ttc | att | ttg | agc | agc | gaa | aac | aga | 864 |
| Leu | Asn | Lys | Thr | Gly | Leu | Leu | Lys | Phe | Ile | Leu | Ser | Ser | Glu | Asn | Arg |     |
|     |     | 275 |     |     |     |     | 280 |     |     |     |     | 285 |     |     |     |     |
| ctt | gaa | tct | ctc | atc | acc | atg | aat | aaa | gaa | ggt | att | ttt | tcg | ttt | att | 912 |
| Leu | Glu | Ser | Leu | Ile | Thr | Met | Asn | Lys | Glu | Gly | Ile | Phe | Ser | Phe | Ile |     |
|     | 290 |     |     |     |     | 295 |     |     |     |     | 300 |     |     |     |     |     |
| gga | tat | ctt | tgt | att | ttt | ata | att | ggt | cag | tct | ttt | ggg | tca | ttt | gtt | 960 |
| Gly | Tyr | Leu | Cys | Ile | Phe | Ile | Ile | Gly | Gln | Ser | Phe | Gly | Ser | Phe | Val |     |
| 305 |     |     |     |     | 310 |     |     |     |     | 315 |     |     |     |     | 320 |     |
| tta | aca | ggc | tac | aaa | aca | aag | aac | aac | tta | ata | acc | att | agc | aaa | att | 1008 |
| Leu | Thr | Gly | Tyr | Lys | Thr | Lys | Asn | Asn | Leu | Ile | Thr | Ile | Ser | Lys | Ile |     |
|     |     |     |     | 325 |     |     |     |     | 330 |     |     |     |     | 335 |     |     |
| cgt | att | tca | aaa | aaa | caa | cac | aag | aaa | gag | ctg | ctg | ctg | ttt | ttc | tca | 1056 |
| Arg | Ile | Ser | Lys | Lys | Gln | His | Lys | Lys | Glu | Leu | Leu | Leu | Phe | Phe | Ser |     |
|     |     |     | 340 |     |     |     |     | 345 |     |     |     |     | 350 |     |     |     |
| gtc | gcc | act | act | cag | gga | tta | tat | ttg | gca | tgt | atc | ttc | tat | cac | tta | 1104 |
| Val | Ala | Thr | Thr | Gln | Gly | Leu | Tyr | Leu | Ala | Cys | Ile | Phe | Tyr | His | Leu |     |
|     |     |     |     | 355 |     |     |     |     | 360 |     |     |     |     | 365 |     |     |
| gct | ttc | agt | ttg | ttc | atc | agc | aac | tta | tca | ttc | ttg | caa | cca | att | tca | 1152 |
| Ala | Phe | Ser | Leu | Phe | Ile | Ser | Asn | Leu | Ser | Phe | Leu | Gln | Pro | Ile | Ser |     |
|     | 370 |     |     |     |     | 375 |     |     |     |     | 380 |     |     |     |     |     |
| aga | cga | ttg | gcc | aat | ttc | ccc | tac | gtc | atg | tgg | gtc | gtt | tcg | tac | aat | 1200 |
| Arg | Arg | Leu | Ala | Asn | Phe | Pro | Tyr | Val | Met | Trp | Val | Val | Ser | Tyr | Asn |     |

```
                385                 390                 395                 400
gct acg ttt tta tta tgt tat gac tta att gaa aaa ttt atc ccg ggg      1248
Ala Thr Phe Leu Leu Cys Tyr Asp Leu Ile Glu Lys Phe Ile Pro Gly
            405                 410                 415 aac ctt act tct act gta ttg gac tct att aat aac aat ggt tta ttt      1296
Asn Leu Thr Ser Thr Val Leu Asp Ser Ile Asn Asn Asn Gly Leu Phe
            420                 425                 430 atc ttc ttg gtc agc aat tta tta aca ggg ttt att aac atg tcc atc      1344
Ile Phe Leu Val Ser Asn Leu Leu Thr Gly Phe Ile Asn Met Ser Ile
            435                 440                 445 aac act ttg gaa act agc aat aaa atg gca gtg att atc ttg att ggc      1392
Asn Thr Leu Glu Thr Ser Asn Lys Met Ala Val Ile Ile Leu Ile Gly
            450                 455                 460 tat agt ctt act tgg aca ttg ctc gcc tta tat ttg gat aag agg aag      1440
Tyr Ser Leu Thr Trp Thr Leu Leu Ala Leu Tyr Leu Asp Lys Arg Lys
465                 470                 475                 480 atc tac atc aag ctt tag                                              1458
Ile Tyr Ile Lys Leu
            485

<210> SEQ ID NO 4
<211> LENGTH: 485
<212> TYPE: PRT
<213> ORGANISM: Candida albicans
<220> FEATURE:
<223> OTHER INFORMATION: GWT1

<400> SEQUENCE: 4

Met Ser Ser Ser Leu Lys Gln Leu Lys Glu Gln Phe Val Ser Asp Leu
 1               5                  10                  15

Thr Gly Gly Thr Ile Glu Glu Ile Tyr Ala Val Thr Ser Ile Ala Leu
                20                  25                  30

Ser Ser Tyr Leu Ser Phe Arg Leu Leu Lys Lys Ser Leu Gly Asp Leu
            35                  40                  45

Ala Leu Ile Tyr Asp Tyr Ile Leu Asn Val Leu Thr Ile Leu Ala Ser
        50                  55                  60

Ile Thr Val Tyr Ser Asn Ser Pro Ser Tyr Leu His Tyr Phe Ile Val
 65                 70                  75                  80

Ile Pro Ser Leu Val Ile Tyr Leu Val Asn Tyr His Val Glu Lys Pro
                85                  90                  95

Ser Ser Pro His Arg Gln Asn Asp Thr Lys Glu Asp Lys Ser Asp Glu
            100                 105                 110

Leu Leu Pro Arg Lys Gln Phe Ile Thr Ala Tyr Arg Ser Gln Met Leu
        115                 120                 125

Ile Ile Thr Asn Leu Ala Ile Leu Ala Val Asp Phe Pro Ile Phe Pro
130                 135                 140

Arg Arg Phe Ala Lys Val Glu Thr Trp Gly Thr Ser Met Met Asp Leu
145                 150                 155                 160

Gly Val Gly Ser Phe Val Ser Met Gly Leu Ala Asn Ser Arg Gln
                165                 170                 175

Leu Ile Lys Asn His Thr Asp Asn Tyr Lys Phe Ser Trp Lys Ser Tyr
            180                 185                 190

Leu Lys Thr Ile Lys Gln Asn Phe Ile Lys Ser Val Pro Ile Leu Val
        195                 200                 205

Leu Gly Ala Ile Arg Phe Val Ser Val Lys Gln Leu Asp Tyr Gln Glu
    210                 215                 220

His Glu Thr Glu Tyr Gly Ile His Trp Asn Phe Phe Thr Leu Gly
225                 230                 235                 240
```

```
Phe Leu Pro Ile Val Leu Gly Ile Leu Asp Pro Val Leu Asn Leu Val
                245                 250                 255

Pro Arg Phe Ile Ile Gly Ile Gly Ile Ser Ile Ala Tyr Glu Val Ala
            260                 265                 270

Leu Asn Lys Thr Gly Leu Leu Lys Phe Ile Leu Ser Ser Glu Asn Arg
        275                 280                 285

Leu Glu Ser Leu Ile Thr Met Asn Lys Glu Gly Ile Phe Ser Phe Ile
    290                 295                 300

Gly Tyr Leu Cys Ile Phe Ile Ile Gly Gln Ser Phe Gly Ser Phe Val
305                 310                 315                 320

Leu Thr Gly Tyr Lys Thr Lys Asn Asn Leu Ile Thr Ile Ser Lys Ile
                325                 330                 335

Arg Ile Ser Lys Lys Gln His Lys Lys Glu Leu Leu Phe Phe Ser
            340                 345                 350

Val Ala Thr Thr Gln Gly Leu Tyr Leu Ala Cys Ile Phe Tyr His Leu
        355                 360                 365

Ala Phe Ser Leu Phe Ile Ser Asn Leu Ser Phe Leu Gln Pro Ile Ser
    370                 375                 380

Arg Arg Leu Ala Asn Phe Pro Tyr Val Met Trp Val Val Ser Tyr Asn
385                 390                 395                 400

Ala Thr Phe Leu Leu Cys Tyr Asp Leu Ile Glu Lys Phe Ile Pro Gly
                405                 410                 415

Asn Leu Thr Ser Thr Val Leu Asp Ser Ile Asn Asn Asn Gly Leu Phe
            420                 425                 430

Ile Phe Leu Val Ser Asn Leu Leu Thr Gly Phe Ile Asn Met Ser Ile
        435                 440                 445

Asn Thr Leu Glu Thr Ser Asn Lys Met Ala Val Ile Ile Leu Ile Gly
    450                 455                 460

Tyr Ser Leu Thr Trp Thr Leu Leu Ala Leu Tyr Leu Asp Lys Arg Lys
465                 470                 475                 480

Ile Tyr Ile Lys Leu
                485

<210> SEQ ID NO 5
<211> LENGTH: 1458
<212> TYPE: DNA
<213> ORGANISM: Candida albicans
<220> FEATURE:
<221> NAME/KEY: CDS
<222> LOCATION: (1)..(1458)
<223> OTHER INFORMATION: GWT1

<400> SEQUENCE: 5 atg tca tcg tct tta aaa caa ttg aaa gaa caa ttt gtc tca gat ttg      48
Met Ser Ser Ser Leu Lys Gln Leu Lys Glu Gln Phe Val Ser Asp Leu
 1               5                  10                  15 act ggt ggc aca att gaa gaa att tat gct gta acc agt ata gca tta      96
Thr Gly Gly Thr Ile Glu Glu Ile Tyr Ala Val Thr Ser Ile Ala Leu
             20                  25                  30 tca tct tat ttg tcc ttt aga ttg ttg aaa aag tct ctt ggt gat tta     144
Ser Ser Tyr Leu Ser Phe Arg Leu Leu Lys Lys Ser Leu Gly Asp Leu
         35                  40                  45 gct ttg att tac gac tac att ctt aat gtg ttg aca att cta gca tcc     192
Ala Leu Ile Tyr Asp Tyr Ile Leu Asn Val Leu Thr Ile Leu Ala Ser
     50                  55                  60 att act gtt tat agc aac agc cct tct tat ttg cat tat ttt att gtt     240
Ile Thr Val Tyr Ser Asn Ser Pro Ser Tyr Leu His Tyr Phe Ile Val
 65                  70                  75                  80
```

```
att cca tca tta gtt ata tat cta gtg aat tac cat gtt gag aaa cca     288
Ile Pro Ser Leu Val Ile Tyr Leu Val Asn Tyr His Val Glu Lys Pro
                85                  90                  95 tct tca ccc cat aga caa aat gat aca aaa gaa gat aaa tcg gac gaa     336
Ser Ser Pro His Arg Gln Asn Asp Thr Lys Glu Asp Lys Ser Asp Glu
            100                 105                 110 cta ttg ccg aga aaa caa ttt ata aca gcc tat cgt tct caa atg ttg     384
Leu Leu Pro Arg Lys Gln Phe Ile Thr Ala Tyr Arg Ser Gln Met Leu
        115                 120                 125 ata att act aat cta gct ata tta gct gtt gat ttt cct att ttc cca     432
Ile Ile Thr Asn Leu Ala Ile Leu Ala Val Asp Phe Pro Ile Phe Pro
    130                 135                 140 aga aga ttt gcc aaa gtg gaa aca tgg ggc acg tca atg atg gat tta     480
Arg Arg Phe Ala Lys Val Glu Thr Trp Gly Thr Ser Met Met Asp Leu
145                 150                 155                 160 gga gtt ggg tcg ttt gtg ttc tcc atg ggg ttg gct aat tct cga caa     528
Gly Val Gly Ser Phe Val Phe Ser Met Gly Leu Ala Asn Ser Arg Gln
                165                 170                 175 ttg atc aag aac cac acc gac aat tac aaa ttt agt tgg aag agt tat     576
Leu Ile Lys Asn His Thr Asp Asn Tyr Lys Phe Ser Trp Lys Ser Tyr
            180                 185                 190 ttg aaa aca atc aag cag aac ttt atc aag tca gtg cct ata ctt gtt     624
Leu Lys Thr Ile Lys Gln Asn Phe Ile Lys Ser Val Pro Ile Leu Val
        195                 200                 205 tta gga gct att cgt ttt gtt agt gtt aag caa ttg gac tat cag gaa     672
Leu Gly Ala Ile Arg Phe Val Ser Val Lys Gln Leu Asp Tyr Gln Glu
    210                 215                 220 cac gaa aca gag tat gga atc cat tgg aat ttt ttc ttc aca tta ggg     720
His Glu Thr Glu Tyr Gly Ile His Trp Asn Phe Phe Phe Thr Leu Gly
225                 230                 235                 240 ttc ttg cca att gta ttg gga ata tta gac ccg gtg ttg aat ttg gtt     768
Phe Leu Pro Ile Val Leu Gly Ile Leu Asp Pro Val Leu Asn Leu Val
                245                 250                 255 cca cgc ttc ata ata gga att ggt atc tca att ggt tat gag gta gcg     816
Pro Arg Phe Ile Ile Gly Ile Gly Ile Ser Ile Gly Tyr Glu Val Ala
            260                 265                 270 ttg aat aag act ggt ttg ttg aag ttc att ttg agc agc gaa aac aga     864
Leu Asn Lys Thr Gly Leu Leu Lys Phe Ile Leu Ser Ser Glu Asn Arg
        275                 280                 285 ctt gaa tct ctc atc gcc atg aat aaa gaa ggt att ttt tcg ttt att     912
Leu Glu Ser Leu Ile Ala Met Asn Lys Glu Gly Ile Phe Ser Phe Ile
    290                 295                 300 gga tat ctt tgt att ttt ata att ggt cag tct ttt ggg tca ttt gtt     960
Gly Tyr Leu Cys Ile Phe Ile Ile Gly Gln Ser Phe Gly Ser Phe Val
305                 310                 315                 320 tta aca ggc tac aaa aca aag aac aac tta ata acc att agc aaa att    1008
Leu Thr Gly Tyr Lys Thr Lys Asn Asn Leu Ile Thr Ile Ser Lys Ile
                325                 330                 335 cgt att tca aaa aaa caa cac aag aaa gag ctg ctg ctg ttt ttc tca    1056
Arg Ile Ser Lys Lys Gln His Lys Lys Glu Leu Leu Leu Phe Phe Ser
            340                 345                 350 gtc gcc act act cag gga tta tat ttg gca tgt atc ttc tat cac tta    1104
Val Ala Thr Thr Gln Gly Leu Tyr Leu Ala Cys Ile Phe Tyr His Leu
        355                 360                 365 gct ttc agt ttg ttc atc agc aac tta tca ttc ttg caa cca att tca    1152
Ala Phe Ser Leu Phe Ile Ser Asn Leu Ser Phe Leu Gln Pro Ile Ser
    370                 375                 380 aga cga ttg gcc aat ttc ccc tac gtc atg tgg gtc gtt tcg tac aat    1200
Arg Arg Leu Ala Asn Phe Pro Tyr Val Met Trp Val Val Ser Tyr Asn
385                 390                 395                 400
```

```
gct acg ttt tta tta tgt tat gac tta att gaa aaa ttt atc ccg ggg      1248
Ala Thr Phe Leu Leu Cys Tyr Asp Leu Ile Glu Lys Phe Ile Pro Gly
            405                 410                 415 aac ctt act tct act gta ttg gac tct att aat aac aat ggt tta ttt      1296
Asn Leu Thr Ser Thr Val Leu Asp Ser Ile Asn Asn Asn Gly Leu Phe
            420                 425                 430 atc ttc ttg gtc agc aat tta tta aca ggg ttt att aac atg tcc atc      1344
Ile Phe Leu Val Ser Asn Leu Leu Thr Gly Phe Ile Asn Met Ser Ile
            435                 440                 445 aac act ttg gaa act agc aat aaa atg gca gtg att atc ttg att ggc      1392
Asn Thr Leu Glu Thr Ser Asn Lys Met Ala Val Ile Ile Leu Ile Gly
            450                 455                 460 tat agt ctt act tgg aca ttg ctc gcc tta tat ttg gat aag agg aag      1440
Tyr Ser Leu Thr Trp Thr Leu Leu Ala Leu Tyr Leu Asp Lys Arg Lys
465                 470                 475                 480 atc tac atc aag ctt tag                                              1458
Ile Tyr Ile Lys Leu
            485

<210> SEQ ID NO 6
<211> LENGTH: 485
<212> TYPE: PRT
<213> ORGANISM: Candida albicans
<220> FEATURE:
<223> OTHER INFORMATION: GWT1

<400> SEQUENCE: 6

Met Ser Ser Ser Leu Lys Gln Leu Lys Glu Gln Phe Val Ser Asp Leu
 1               5                  10                  15

Thr Gly Gly Thr Ile Glu Glu Ile Tyr Ala Val Thr Ser Ile Ala Leu
            20                  25                  30

Ser Ser Tyr Leu Ser Phe Arg Leu Leu Lys Ser Leu Gly Asp Leu
        35                  40                  45

Ala Leu Ile Tyr Asp Tyr Ile Leu Asn Val Leu Thr Ile Leu Ala Ser
    50                  55                  60

Ile Thr Val Tyr Ser Asn Ser Pro Ser Tyr Leu His Tyr Phe Ile Val
65                  70                  75                  80

Ile Pro Ser Leu Val Ile Tyr Leu Val Asn Tyr His Val Glu Lys Pro
                85                  90                  95

Ser Ser Pro His Arg Gln Asn Asp Thr Lys Glu Asp Lys Ser Asp Glu
            100                 105                 110

Leu Leu Pro Arg Lys Gln Phe Ile Thr Ala Tyr Arg Ser Gln Met Leu
        115                 120                 125

Ile Ile Thr Asn Leu Ala Ile Leu Ala Val Asp Phe Pro Ile Phe Pro
    130                 135                 140

Arg Arg Phe Ala Lys Val Glu Thr Trp Gly Thr Ser Met Met Asp Leu
145                 150                 155                 160

Gly Val Gly Ser Phe Val Phe Ser Met Gly Leu Ala Asn Ser Arg Gln
                165                 170                 175

Leu Ile Lys Asn His Thr Asp Asn Tyr Lys Phe Ser Trp Lys Ser Tyr
            180                 185                 190

Leu Lys Thr Ile Lys Gln Asn Phe Ile Lys Ser Val Pro Ile Leu Val
        195                 200                 205

Leu Gly Ala Ile Arg Phe Val Ser Val Lys Gln Leu Asp Tyr Gln Glu
    210                 215                 220

His Glu Thr Glu Tyr Gly Ile His Trp Asn Phe Phe Phe Thr Leu Gly
225                 230                 235                 240
```

```
                                  -continued
        Phe Leu Pro Ile Val Leu Gly Ile Leu Asp Pro Val Leu Asn Leu Val
                        245                 250                 255

Pro Arg Phe Ile Ile Gly Ile Gly Ile Ser Ile Gly Tyr Glu Val Ala
                    260                 265                 270

Leu Asn Lys Thr Gly Leu Leu Lys Phe Ile Leu Ser Ser Glu Asn Arg
                275                 280                 285

Leu Glu Ser Leu Ile Ala Met Asn Lys Glu Gly Ile Phe Ser Phe Ile
            290                 295                 300

Gly Tyr Leu Cys Ile Phe Ile Ile Gly Gln Ser Phe Gly Ser Phe Val
        305                 310                 315                 320

Leu Thr Gly Tyr Lys Thr Lys Asn Asn Leu Ile Thr Ile Ser Lys Ile
                        325                 330                 335

Arg Ile Ser Lys Lys Gln His Lys Lys Glu Leu Leu Leu Phe Phe Ser
                    340                 345                 350

Val Ala Thr Thr Gln Gly Leu Tyr Leu Ala Cys Ile Phe Tyr His Leu
                355                 360                 365

Ala Phe Ser Leu Phe Ile Ser Asn Leu Ser Phe Leu Gln Pro Ile Ser
            370                 375                 380

Arg Arg Leu Ala Asn Phe Pro Tyr Val Met Trp Val Ser Tyr Asn
        385                 390                 395                 400

Ala Thr Phe Leu Leu Cys Tyr Asp Leu Ile Glu Lys Phe Ile Pro Gly
                        405                 410                 415

Asn Leu Thr Ser Thr Val Leu Asp Ser Ile Asn Asn Gly Leu Phe
                    420                 425                 430

Ile Phe Leu Val Ser Asn Leu Leu Thr Gly Phe Ile Asn Met Ser Ile
                435                 440                 445

Asn Thr Leu Glu Thr Ser Asn Lys Met Ala Val Ile Ile Leu Ile Gly
            450                 455                 460

Tyr Ser Leu Thr Trp Thr Leu Leu Ala Leu Tyr Leu Asp Lys Arg Lys
        465                 470                 475                 480

Ile Tyr Ile Lys Leu
                        485

<210> SEQ ID NO 7
<211> LENGTH: 1380
<212> TYPE: DNA
<213> ORGANISM: Schizosaccharomyces pombe
<220> FEATURE:
<221> NAME/KEY: CDS
<222> LOCATION: (1)..(1380)
<223> OTHER INFORMATION: GWT1

<400> SEQUENCE: 7 atg tca tac aaa ttg gaa aaa gaa gca ttt gtc tca aac ctg acg ggt      48
Met Ser Tyr Lys Leu Glu Lys Glu Ala Phe Val Ser Asn Leu Thr Gly
 1               5                  10                  15 tca agt tcc att gag aca tgt ggc ttg tta tta ata gga att gct tgc     96
Ser Ser Ser Ile Glu Thr Cys Gly Leu Leu Leu Ile Gly Ile Ala Cys
                20                  25                  30 aac gtt ttg tgg gta aac atg act gcg aga aac atc tta ccc aaa ggg    144
Asn Val Leu Trp Val Asn Met Thr Ala Arg Asn Ile Leu Pro Lys Gly
            35                  40                  45 aat ctt ggg ttt ctt gtt gag ttt ttc atc ttt tgc tta att cca tta    192
Asn Leu Gly Phe Leu Val Glu Phe Phe Ile Phe Cys Leu Ile Pro Leu
        50                  55                  60 ttt gtc att tac gtt tca tcg aaa gtt ggc gtt ttc act ctt tgc ata    240
Phe Val Ile Tyr Val Ser Ser Lys Val Gly Val Phe Thr Leu Cys Ile
 65                  70                  75                  80
```

| | | |
|---|---|---|
| gcc tct ttt ttg cct tcc ttc gtc ctt cat gtt ata agt cca att aat<br>Ala Ser Phe Leu Pro Ser Phe Val Leu His Val Ile Ser Pro Ile Asn<br>               85                      90                 95 | | 288 |
| tgg gat gtg ctg aga aga aaa cct ggt tgt tgt ctt act aaa aaa aat<br>Trp Asp Val Leu Arg Arg Lys Pro Gly Cys Cys Leu Thr Lys Lys Asn<br>              100                   105               110 | | 336 |
| gaa aat act ttt gat cga cga att gct gga gtc aca ttt tat cgt tct<br>Glu Asn Thr Phe Asp Arg Arg Ile Ala Gly Val Thr Phe Tyr Arg Ser<br>              115                   120               125 | | 384 |
| caa atg atg ttg gtt act gtc act tgc atc ctg gcc gtt gac ttt acc<br>Gln Met Met Leu Val Thr Val Thr Cys Ile Leu Ala Val Asp Phe Thr<br>    130                   135               140 | | 432 |
| ctt ttc ccg agg aga tat gcc aaa gtt gaa acc tgg gga aca tca ctg<br>Leu Phe Pro Arg Arg Tyr Ala Lys Val Glu Thr Trp Gly Thr Ser Leu<br>145                  150               155             160 | | 480 |
| atg gat ctt ggt gtt gga tct ttc atg ttt tct tca ggt act gtg gct<br>Met Asp Leu Gly Val Gly Ser Phe Met Phe Ser Ser Gly Thr Val Ala<br>              165                   170               175 | | 528 |
| gga cgg aaa aat gac att aaa aaa cca aat gcg ttt aaa aat gta ttg<br>Gly Arg Lys Asn Asp Ile Lys Lys Pro Asn Ala Phe Lys Asn Val Leu<br>            180                   185               190 | | 576 |
| tgg aat tct ttc atc ctt ttg att tta gga ttt gcg cgc atg ttt tta<br>Trp Asn Ser Phe Ile Leu Leu Ile Leu Gly Phe Ala Arg Met Phe Leu<br>        195               200               205 | | 624 |
| acg aaa agc atc aat tac caa gaa cat gta agc gaa tat ggc atg cat<br>Thr Lys Ser Ile Asn Tyr Gln Glu His Val Ser Glu Tyr Gly Met His<br>210                  215               220 | | 672 |
| tgg aac ttt ttt ttc acc cta ggt ttc atg gct ctt ggc gta ttt ttt<br>Trp Asn Phe Phe Phe Thr Leu Gly Phe Met Ala Leu Gly Val Phe Phe<br>225                  230               235             240 | | 720 |
| ttt cgt cgt tct tta aaa aaa gtc tcc tat ttt aat tta gca acc ttc<br>Phe Arg Arg Ser Leu Lys Lys Val Ser Tyr Phe Asn Leu Ala Thr Phe<br>              245                   250               255 | | 768 |
| att act ctt ctt cat cat tgt ttg ctt gtt tta acc cct ttc caa aaa<br>Ile Thr Leu Leu His His Cys Leu Leu Val Leu Thr Pro Phe Gln Lys<br>            260                   265               270 | | 816 |
| tgg gca cta tcc gcc ccc aga aca aat att ttg gct cag aat aga gag<br>Trp Ala Leu Ser Ala Pro Arg Thr Asn Ile Leu Ala Gln Asn Arg Glu<br>        275               280               285 | | 864 |
| ggt att gct tct ctt ccc gga tac att gct att tac ttt tat gga atg<br>Gly Ile Ala Ser Leu Pro Gly Tyr Ile Ala Ile Tyr Phe Tyr Gly Met<br>    290                   295               300 | | 912 |
| tat acc ggt agt gta gtt ttg gct gat cga cct cta atg tat act aga<br>Tyr Thr Gly Ser Val Val Leu Ala Asp Arg Pro Leu Met Tyr Thr Arg<br>305                  310               315             320 | | 960 |
| gct gag tcg tgg aag cgc ttt caa cgt cta tta ttc ccg cta tgc att<br>Ala Glu Ser Trp Lys Arg Phe Gln Arg Leu Leu Phe Pro Leu Cys Ile<br>              325                   330               335 | | 1008 |
| ttg tta gtg ttg tat ctt gtg tct aac ttt ttg tca gtt ggt gtt tct<br>Leu Leu Val Leu Tyr Leu Val Ser Asn Phe Leu Ser Val Gly Val Ser<br>        340             345               350 | | 1056 |
| cgc cga ctt gct aat acg cct tat gtt gcg aat gtt gcc ttt atc aat<br>Arg Arg Leu Ala Asn Thr Pro Tyr Val Ala Asn Val Ala Phe Ile Asn<br>        355               360               365 | | 1104 |
| atg ttt ttt ctt act ata tac ata ctt att gat gcc tat tta ttc cca<br>Met Phe Phe Leu Thr Ile Tyr Ile Leu Ile Asp Ala Tyr Leu Phe Pro<br>    370                   375               380 | | 1152 |
| tct tct gtg cca tat gga agt cgc gtc ccc aaa ctg ctt gaa gat gcc<br>Ser Ser Val Pro Tyr Gly Ser Arg Val Pro Lys Leu Leu Glu Asp Ala<br>385                  390               395             400 | | 1200 |

```
aat aat aat ggc ttg ttg gtg ttt ttg att gct aac gtt tta aca gga       1248
Asn Asn Asn Gly Leu Leu Val Phe Leu Ile Ala Asn Val Leu Thr Gly
            405                 410                 415 gta gtt aat tta tcg ttc gac acc ctt cat tct agc aat gca aaa ggc       1296
Val Val Asn Leu Ser Phe Asp Thr Leu His Ser Ser Asn Ala Lys Gly
            420                 425                 430 ttg aca atc atg act atg tat ctt ttt att att tgc tat atg gca cat       1344
Leu Thr Ile Met Thr Met Tyr Leu Phe Ile Ile Cys Tyr Met Ala His
            435                 440                 445 tgg ctt gct caa cac gga att cgt ttt cgc ctt tag                       1380
Trp Leu Ala Gln His Gly Ile Arg Phe Arg Leu
            450                 455
```

<210> SEQ ID NO 8
<211> LENGTH: 459
<212> TYPE: PRT
<213> ORGANISM: Schizosaccharomyces pombe
<220> FEATURE:
<223> OTHER INFORMATION: GWT1

<400> SEQUENCE: 8

```
Met Ser Tyr Lys Leu Glu Lys Glu Ala Phe Val Ser Asn Leu Thr Gly
  1               5                  10                  15

Ser Ser Ser Ile Glu Thr Cys Gly Leu Leu Ile Gly Ile Ala Cys
                 20                  25                  30

Asn Val Leu Trp Val Asn Met Thr Ala Arg Asn Ile Leu Pro Lys Gly
             35                  40                  45

Asn Leu Gly Phe Leu Val Glu Phe Phe Ile Phe Cys Leu Ile Pro Leu
         50                  55                  60

Phe Val Ile Tyr Val Ser Ser Lys Val Gly Val Phe Thr Leu Cys Ile
 65                  70                  75                  80

Ala Ser Phe Leu Pro Ser Phe Val Leu His Val Ile Ser Pro Ile Asn
                 85                  90                  95

Trp Asp Val Leu Arg Arg Lys Pro Gly Cys Cys Leu Thr Lys Lys Asn
            100                 105                 110

Glu Asn Thr Phe Asp Arg Arg Ile Ala Gly Val Thr Phe Tyr Arg Ser
        115                 120                 125

Gln Met Met Leu Val Thr Val Thr Cys Ile Leu Ala Val Asp Phe Thr
    130                 135                 140

Leu Phe Pro Arg Arg Tyr Ala Lys Val Glu Thr Trp Gly Thr Ser Leu
145                 150                 155                 160

Met Asp Leu Gly Val Gly Ser Phe Met Phe Ser Ser Gly Thr Val Ala
                165                 170                 175

Gly Arg Lys Asn Asp Ile Lys Lys Pro Asn Ala Phe Lys Asn Val Leu
            180                 185                 190

Trp Asn Ser Phe Ile Leu Leu Ile Leu Gly Phe Ala Arg Met Phe Leu
        195                 200                 205

Thr Lys Ser Ile Asn Tyr Gln Glu His Val Ser Glu Tyr Gly Met His
    210                 215                 220

Trp Asn Phe Phe Phe Thr Leu Gly Phe Met Ala Leu Gly Val Phe Phe
225                 230                 235                 240

Phe Arg Arg Ser Leu Lys Lys Val Ser Tyr Phe Asn Leu Ala Thr Phe
                245                 250                 255

Ile Thr Leu Leu His His Cys Leu Leu Val Leu Thr Pro Phe Gln Lys
            260                 265                 270

Trp Ala Leu Ser Ala Pro Arg Thr Asn Ile Leu Ala Gln Asn Arg Glu
        275                 280                 285
```

```
Gly Ile Ala Ser Leu Pro Gly Tyr Ile Ala Ile Tyr Phe Tyr Gly Met
            290                 295                 300

Tyr Thr Gly Ser Val Val Leu Ala Asp Arg Pro Leu Met Tyr Thr Arg
305                 310                 315                 320

Ala Glu Ser Trp Lys Arg Phe Gln Arg Leu Leu Phe Pro Leu Cys Ile
                325                 330                 335

Leu Leu Val Leu Tyr Leu Val Ser Asn Phe Leu Ser Val Gly Val Ser
            340                 345                 350

Arg Arg Leu Ala Asn Thr Pro Tyr Val Ala Asn Val Ala Phe Ile Asn
                355                 360                 365

Met Phe Phe Leu Thr Ile Tyr Ile Leu Ile Asp Ala Tyr Leu Phe Pro
            370                 375                 380

Ser Ser Val Pro Tyr Gly Ser Arg Val Pro Lys Leu Leu Glu Asp Ala
385                 390                 395                 400

Asn Asn Asn Gly Leu Leu Val Phe Leu Ile Ala Asn Val Leu Thr Gly
                405                 410                 415

Val Val Asn Leu Ser Phe Asp Thr Leu His Ser Ser Asn Ala Lys Gly
            420                 425                 430

Leu Thr Ile Met Thr Met Tyr Leu Phe Ile Ile Cys Tyr Met Ala His
            435                 440                 445

Trp Leu Ala Gln His Gly Ile Arg Phe Arg Leu
    450                 455

<210> SEQ ID NO 9
<211> LENGTH: 1576
<212> TYPE: DNA
<213> ORGANISM: Aspergillus fumigatus
<220> FEATURE:
<221> NAME/KEY: CDS
<222> LOCATION: (31)..(1536)
<223> OTHER INFORMATION: GWT1

<400> SEQUENCE: 9
aaggtgcaaa tcccgcggca ttgagtcaag atg gat cca gat tat aaa gct cgc        54
                                 Met Asp Pro Asp Tyr Lys Ala Arg
                                   1               5 aaa gag gcc ttt gtc tca ggt ctt gca gga gga agc atc ctg gaa atc       102
Lys Glu Ala Phe Val Ser Gly Leu Ala Gly Gly Ser Ile Leu Glu Ile
         10                  15                  20 aac gcc gtc acc ttg gtt gct tcg gta tcc gtt ttt ctg tgg tca att       150
Asn Ala Val Thr Leu Val Ala Ser Val Ser Val Phe Leu Trp Ser Ile
 25                  30                  35                  40 cta caa tct cgc cta tcc ttt ttc aca ccc tac agc gcc gct gcc ctt       198
Leu Gln Ser Arg Leu Ser Phe Phe Thr Pro Tyr Ser Ala Ala Ala Leu
                 45                  50                  55 ctc gtt gat ttc ctg ctc aat gta cta gct atc ttg ttc gca acc act       246
Leu Val Asp Phe Leu Leu Asn Val Leu Ala Ile Leu Phe Ala Thr Thr
             60                  65                  70 tta tac tct tcg gcg cct ctt ctt ctc aat ctc ctt cta ata tct ccc       294
Leu Tyr Ser Ser Ala Pro Leu Leu Leu Asn Leu Leu Leu Ile Ser Pro
         75                  80                  85 gct ctg ctg ata ctc ctc tct acg aaa cgt cct cgg acc ccc gtc aaa       342
Ala Leu Leu Ile Leu Leu Ser Thr Lys Arg Pro Arg Thr Pro Val Lys
 90                  95                 100 gcg aaa cct cct cgc cag tcc gct aga gct ggg aaa gat gac tcg aaa       390
Ala Lys Pro Pro Arg Gln Ser Ala Arg Ala Gly Lys Asp Asp Ser Lys
105                 110                 115                 120 cat gcg aca gcc ttg cca gag tct cta ccc att cat cca ttt ctc acg       438
His Ala Thr Ala Leu Pro Glu Ser Leu Pro Ile His Pro Phe Leu Thr
                125                 130                 135
```

| | | | | | | | | | | | | | | | | |
|---|---|---|---|---|---|---|---|---|---|---|---|---|---|---|---|---|
| aca | tat | cgc | gcc | gcc | atg | atg | gtt | atc | acg | tgc | atc | gct | atc | ttg | gct | 486 |
| Thr | Tyr | Arg | Ala | Ala | Met | Met | Val | Ile | Thr | Cys | Ile | Ala | Ile | Leu | Ala | |
| | | 140 | | | | 145 | | | | | 150 | | | | | |
| gtg | gat | ttt | cgc | att | ttt | cct | cgc | cga | ttc | gcc | aag | gta | gaa | aac | tgg | 534 |
| Val | Asp | Phe | Arg | Ile | Phe | Pro | Arg | Arg | Phe | Ala | Lys | Val | Glu | Asn | Trp | |
| | | | 155 | | | | | 160 | | | | | 165 | | | |
| ggt | aca | tca | ctc | atg | gat | ctg | ggc | gtt | gga | tcg | ttt | gtc | ttt | tcg | ggc | 582 |
| Gly | Thr | Ser | Leu | Met | Asp | Leu | Gly | Val | Gly | Ser | Phe | Val | Phe | Ser | Gly | |
| 170 | | | | | 175 | | | | | 180 | | | | | | |
| gga | gta | gta | tcc | gct | cgc | tca | cta | ctc | aag | agc | agg | acc | aat | ggc | tct | 630 |
| Gly | Val | Val | Ser | Ala | Arg | Ser | Leu | Leu | Lys | Ser | Arg | Thr | Asn | Gly | Ser | |
| 185 | | | | 190 | | | | | 195 | | | | | 200 | | |
| aaa | agg | ttg | cct | ctt | gcc | aag | agg | ttg | att | gcg | tcg | acg | cga | cac | tct | 678 |
| Lys | Arg | Leu | Pro | Leu | Ala | Lys | Arg | Leu | Ile | Ala | Ser | Thr | Arg | His | Ser | |
| | | | | 205 | | | | | 210 | | | | | 215 | | |
| att | cct | ctg | ctc | gtc | ctc | ggc | ctg | att | cgg | cta | tac | agc | gtc | aaa | ggc | 726 |
| Ile | Pro | Leu | Leu | Val | Leu | Gly | Leu | Ile | Arg | Leu | Tyr | Ser | Val | Lys | Gly | |
| | | | 220 | | | | | 225 | | | | | 230 | | | |
| ttg | gac | tat | gcg | gag | cac | gtc | acc | gag | tac | ggc | gta | cat | tgg | aac | ttc | 774 |
| Leu | Asp | Tyr | Ala | Glu | His | Val | Thr | Glu | Tyr | Gly | Val | His | Trp | Asn | Phe | |
| | | | 235 | | | | | 240 | | | | | 245 | | | |
| ttc | ttt | aca | ttg | ggt | ctt | ttg | cct | ccg | ttc | gtg | gag | gtc | ttc | gac | gcc | 822 |
| Phe | Phe | Thr | Leu | Gly | Leu | Leu | Pro | Pro | Phe | Val | Glu | Val | Phe | Asp | Ala | |
| | 250 | | | | | 255 | | | | | 260 | | | | | |
| ttg | gct | acg | atc | att | ccg | tca | tac | gag | gtt | ctc | tcc | gtg | ggg | atc | gcc | 870 |
| Leu | Ala | Thr | Ile | Ile | Pro | Ser | Tyr | Glu | Val | Leu | Ser | Val | Gly | Ile | Ala | |
| 265 | | | | | 270 | | | | | 275 | | | | | 280 | |
| gtc | ttg | tat | caa | gtt | gcc | cta | gag | tca | aca | gac | ttg | aaa | agc | tac | atc | 918 |
| Val | Leu | Tyr | Gln | Val | Ala | Leu | Glu | Ser | Thr | Asp | Leu | Lys | Ser | Tyr | Ile | |
| | | | | 285 | | | | | 290 | | | | | 295 | | |
| ctc | gtc | tcc | cct | cgt | ggg | cca | agc | tta | ctg | tcc | aag | aat | cgt | gaa | ggc | 966 |
| Leu | Val | Ser | Pro | Arg | Gly | Pro | Ser | Leu | Leu | Ser | Lys | Asn | Arg | Glu | Gly | |
| | | | 300 | | | | | 305 | | | | | 310 | | | |
| gtc | ttc | tcc | ttc | tca | ggt | tat | ctc | gcg | att | ttt | ctt | gct | ggt | cgt | gcg | 1014 |
| Val | Phe | Ser | Phe | Ser | Gly | Tyr | Leu | Ala | Ile | Phe | Leu | Ala | Gly | Arg | Ala | |
| | | | 315 | | | | | 320 | | | | | 325 | | | |
| atc | ggc | att | cgg | ata | atc | cct | cgc | gga | act | tct | ttc | tca | aga | agc | cca | 1062 |
| Ile | Gly | Ile | Arg | Ile | Ile | Pro | Arg | Gly | Thr | Ser | Phe | Ser | Arg | Ser | Pro | |
| | 330 | | | | | 335 | | | | | 340 | | | | | |
| gaa | cag | gcc | agg | aga | cgg | gtc | ctg | atc | agc | ctt | ggc | gtg | caa | gcg | tta | 1110 |
| Glu | Gln | Ala | Arg | Arg | Arg | Val | Leu | Ile | Ser | Leu | Gly | Val | Gln | Ala | Leu | |
| 345 | | | | | 350 | | | | | 355 | | | | | 360 | |
| gtg | tgg | acc | act | ctt | ttt | gtg | ttg | aac | tcc | act | tat | gcg | atg | gga | tac | 1158 |
| Val | Trp | Thr | Thr | Leu | Phe | Val | Leu | Asn | Ser | Thr | Tyr | Ala | Met | Gly | Tyr | |
| | | | | 365 | | | | | 370 | | | | | 375 | | |
| gga | gct | aat | atc | cct | gtc | tcc | cgc | cgc | ctc | gct | aac | atg | ccc | tat | gtc | 1206 |
| Gly | Ala | Asn | Ile | Pro | Val | Ser | Arg | Arg | Leu | Ala | Asn | Met | Pro | Tyr | Val | |
| | | | 380 | | | | | 385 | | | | | 390 | | | |
| ctt | tgg | gtt | tcg | gcg | ttc | aac | acc | gcg | caa | ctg | ttt | gtg | ttc | tgc | ctg | 1254 |
| Leu | Trp | Val | Ser | Ala | Phe | Asn | Thr | Ala | Gln | Leu | Phe | Val | Phe | Cys | Leu | |
| | | | 395 | | | | | 400 | | | | | 405 | | | |
| atc | gaa | aca | ctc | tgc | ttt | cct | gca | gtt | cat | cgg | aca | acg | act | caa | gag | 1302 |
| Ile | Glu | Thr | Leu | Cys | Phe | Pro | Ala | Val | His | Arg | Thr | Thr | Thr | Gln | Glu | |
| | 410 | | | | | 415 | | | | | 420 | | | | | |
| agc | gaa | tct | gag | cga | gtc | gat | ttt | gct | acg | agc | cga | atc | atg | tcg | gcc | 1350 |
| Ser | Glu | Ser | Glu | Arg | Val | Asp | Phe | Ala | Thr | Ser | Arg | Ile | Met | Ser | Ala | |
| 425 | | | | | 430 | | | | | 435 | | | | | 440 | |
| ttc | aat | aag | aac | agt | ctc | gcg | atc | ttt | ctt | ttg | gcc | aat | ctt | ctg | act | 1398 |
| Phe | Asn | Lys | Asn | Ser | Leu | Ala | Ile | Phe | Leu | Leu | Ala | Asn | Leu | Leu | Thr | |
| | | | | 445 | | | | | 450 | | | | | 455 | | |

```
gga gct gtg aat ctg agc atc tcc aca att gat gct aat aca gcg cag    1446
Gly Ala Val Asn Leu Ser Ile Ser Thr Ile Asp Ala Asn Thr Ala Gln
            460                 465                 470 gcc atc gct gtt ctc att gga tat tca tcc att atc aca ggg gtt gct    1494
Ala Ile Ala Val Leu Ile Gly Tyr Ser Ser Ile Ile Thr Gly Val Ala
        475                 480                 485 cta gca ttg cat cat gcc aat atc aaa gta ctt cct ttc tag            1536
Leu Ala Leu His His Ala Asn Ile Lys Val Leu Pro Phe
    490                 495                 500 ggtatttacg agcaattggt ggtgtgttga agatatatag                        1576

<210> SEQ ID NO 10
<211> LENGTH: 501
<212> TYPE: PRT
<213> ORGANISM: Aspergillus fumigatus
<220> FEATURE:
<223> OTHER INFORMATION: GWT1

<400> SEQUENCE: 10

Met Asp Pro Asp Tyr Lys Ala Arg Lys Glu Ala Phe Val Ser Gly Leu
 1               5                  10                  15

Ala Gly Gly Ser Ile Leu Glu Ile Asn Ala Val Thr Leu Val Ala Ser
            20                  25                  30

Val Ser Val Phe Leu Trp Ser Ile Leu Gln Ser Arg Leu Ser Phe Phe
        35                  40                  45

Thr Pro Tyr Ser Ala Ala Ala Leu Leu Val Asp Phe Leu Leu Asn Val
    50                  55                  60

Leu Ala Ile Leu Phe Ala Thr Thr Leu Tyr Ser Ser Ala Pro Leu Leu
65                  70                  75                  80

Leu Asn Leu Leu Leu Ile Ser Pro Ala Leu Ile Leu Leu Ser Thr
                85                  90                  95

Lys Arg Pro Arg Thr Pro Val Lys Ala Lys Pro Pro Arg Gln Ser Ala
            100                 105                 110

Arg Ala Gly Lys Asp Asp Ser Lys His Ala Thr Ala Leu Pro Glu Ser
        115                 120                 125

Leu Pro Ile His Pro Phe Leu Thr Thr Tyr Arg Ala Ala Met Met Val
    130                 135                 140

Ile Thr Cys Ile Ala Ile Leu Ala Val Asp Phe Arg Ile Phe Pro Arg
145                 150                 155                 160

Arg Phe Ala Lys Val Glu Asn Trp Gly Thr Ser Leu Met Asp Leu Gly
                165                 170                 175

Val Gly Ser Phe Val Phe Ser Gly Gly Val Ser Ala Arg Ser Leu
            180                 185                 190

Leu Lys Ser Arg Thr Asn Gly Ser Lys Arg Leu Pro Ala Lys Arg
        195                 200                 205

Leu Ile Ala Ser Thr Arg His Ser Ile Pro Leu Leu Val Leu Gly Leu
    210                 215                 220

Ile Arg Leu Tyr Ser Val Lys Gly Leu Asp Tyr Ala Glu His Val Thr
225                 230                 235                 240

Glu Tyr Gly Val His Trp Asn Phe Phe Thr Leu Gly Leu Leu Pro
                245                 250                 255

Pro Phe Val Glu Val Phe Asp Ala Leu Ala Thr Ile Ile Pro Ser Tyr
            260                 265                 270

Glu Val Leu Ser Val Gly Ile Ala Val Leu Tyr Gln Val Ala Leu Glu
        275                 280                 285

Ser Thr Asp Leu Lys Ser Tyr Ile Leu Val Ser Pro Arg Gly Pro Ser
```

```
                    290                 295                 300
Leu Leu Ser Lys Asn Arg Glu Val Phe Ser Phe Ser Gly Tyr Leu
305                 310                 315                 320

Ala Ile Phe Leu Ala Gly Arg Ala Ile Gly Ile Arg Ile Ile Pro Arg
                325                 330                 335

Gly Thr Ser Phe Ser Arg Ser Pro Glu Gln Ala Arg Arg Val Leu
                340                 345                 350

Ile Ser Leu Gly Val Gln Ala Leu Val Trp Thr Thr Leu Phe Val Leu
                355                 360                 365

Asn Ser Thr Tyr Ala Met Gly Tyr Gly Ala Asn Ile Pro Val Ser Arg
370                 375                 380

Arg Leu Ala Asn Met Pro Tyr Val Leu Trp Val Ser Ala Phe Asn Thr
385                 390                 395                 400

Ala Gln Leu Phe Val Phe Cys Leu Ile Glu Thr Leu Cys Phe Pro Ala
                405                 410                 415

Val His Arg Thr Thr Thr Gln Glu Ser Glu Ser Glu Val Asp Phe
                420                 425                 430

Ala Thr Ser Arg Ile Met Ser Ala Phe Asn Lys Asn Ser Leu Ala Ile
                435                 440                 445

Phe Leu Leu Ala Asn Leu Leu Thr Gly Ala Val Asn Leu Ser Ile Ser
450                 455                 460

Thr Ile Asp Ala Asn Thr Ala Gln Ala Ile Ala Val Leu Ile Gly Tyr
465                 470                 475                 480

Ser Ser Ile Ile Thr Gly Val Ala Leu Ala Leu His His Ala Asn Ile
                485                 490                 495

Lys Val Leu Pro Phe
                500

<210> SEQ ID NO 11
<211> LENGTH: 1648
<212> TYPE: DNA
<213> ORGANISM: Aspergillus fumigatus
<220> FEATURE:
<221> NAME/KEY: CDS
<222> LOCATION: (26)..(121)
<223> OTHER INFORMATION: GWT1
<220> FEATURE:
<221> NAME/KEY: CDS
<222> LOCATION: (199)..(1608)
<223> OTHER INFORMATION: GWT1
<220> FEATURE:
<221> NAME/KEY: exon
<222> LOCATION: (26)..(121)
<220> FEATURE:
<221> NAME/KEY: intron
<222> LOCATION: (122)..(198)
<220> FEATURE:
<221> NAME/KEY: exon
<222> LOCATION: (199)..(1608)

<400> SEQUENCE: 11
gcaaatcccg cggcattgag tcaag atg gat cca gat tat aaa gct cgc aaa        52
                          Met Asp Pro Asp Tyr Lys Ala Arg Lys
                           1               5 gag gcc ttt gtc tca ggt ctt gca gga gga agc atc ctg gaa atc aac       100
Glu Ala Phe Val Ser Gly Leu Ala Gly Gly Ser Ile Leu Glu Ile Asn
 10              15                  20                  25 gcc gtc acc ttg gtt gct tcg gttcgtgtta ctatcttatt gtggctactt          151
Ala Val Thr Leu Val Ala Ser
                30 cgcctacatt gtttctcgac taaccgagtc tctttgcgat caatcag gta tcc gtt       207
                                                    Val Ser Val
```

|   |   |   |   |   |   |   |   |   |   |   |   |   |   |   |   |     |
|---|---|---|---|---|---|---|---|---|---|---|---|---|---|---|---|-----|
| ttt | ctg | tgg | tca | att | cta | caa | tct | cgc | cta | tcc | ttt | ttc | aca | ccc | tac | 255 |
| Phe | Leu | Trp | Ser | Ile | Leu | Gln | Ser | Arg | Leu | Ser | Phe | Phe | Thr | Pro | Tyr |     |
|     |     |     | 40  |     |     |     |     | 45  |     |     |     |     | 50  |     |     |     |
| agc | gcc | gct | gcc | ctt | ctc | gtt | gat | ttc | ctg | ctc | aat | gta | cta | gct | atc | 303 |
| Ser | Ala | Ala | Ala | Leu | Leu | Val | Asp | Phe | Leu | Leu | Asn | Val | Leu | Ala | Ile |     |
|     |     | 55  |     |     |     |     | 60  |     |     |     |     | 65  |     |     |     |     |
| ttg | ttc | gca | acc | act | tta | tac | tct | tcg | gcg | cct | ctt | ctt | ctc | aat | ctc | 351 |
| Leu | Phe | Ala | Thr | Thr | Leu | Tyr | Ser | Ser | Ala | Pro | Leu | Leu | Leu | Asn | Leu |     |
|     | 70  |     |     |     |     | 75  |     |     |     |     | 80  |     |     |     |     |     |
| ctt | cta | ata | tct | ccc | gct | ctg | ctg | ata | ctc | ctc | tct | acg | aaa | cgt | cct | 399 |
| Leu | Leu | Ile | Ser | Pro | Ala | Leu | Leu | Ile | Leu | Leu | Ser | Thr | Lys | Arg | Pro |     |
| 85  |     |     |     |     | 90  |     |     |     |     | 95  |     |     |     |     |     |     |
| cgg | acc | ccc | gtc | aaa | gcg | aaa | cct | cct | cgc | cag | tcc | gct | aga | gct | ggg | 447 |
| Arg | Thr | Pro | Val | Lys | Ala | Lys | Pro | Pro | Arg | Gln | Ser | Ala | Arg | Ala | Gly |     |
| 100 |     |     |     | 105 |     |     |     | 110 |     |     |     | 115 |     |     |     |     |
| aaa | gat | gac | tcg | aaa | cat | gcg | aca | gcc | ttg | cca | gag | tct | cta | ccc | att | 495 |
| Lys | Asp | Asp | Ser | Lys | His | Ala | Thr | Ala | Leu | Pro | Glu | Ser | Leu | Pro | Ile |     |
|     |     |     | 120 |     |     |     | 125 |     |     |     | 130 |     |     |     |     |     |
| cat | cca | ttt | ctc | acg | aca | tat | cgc | gcc | gcc | atg | atg | gtt | atc | acg | tgc | 543 |
| His | Pro | Phe | Leu | Thr | Thr | Tyr | Arg | Ala | Ala | Met | Met | Val | Ile | Thr | Cys |     |
|     |     | 135 |     |     |     | 140 |     |     |     | 145 |     |     |     |     |     |     |
| atc | gct | atc | ttg | gct | gtg | gat | ttt | cgc | att | ttt | cct | cgc | cga | ttc | gcc | 591 |
| Ile | Ala | Ile | Leu | Ala | Val | Asp | Phe | Arg | Ile | Phe | Pro | Arg | Arg | Phe | Ala |     |
|     | 150 |     |     |     | 155 |     |     |     | 160 |     |     |     |     |     |     |     |
| aag | gta | gaa | aac | tgg | ggt | aca | tca | ctc | atg | gat | ctg | ggc | gtt | gga | tcg | 639 |
| Lys | Val | Glu | Asn | Trp | Gly | Thr | Ser | Leu | Met | Asp | Leu | Gly | Val | Gly | Ser |     |
|     | 165 |     |     |     | 170 |     |     |     | 175 |     |     |     |     |     |     |     |
| ttt | gtc | ttt | tcg | ggc | gga | gta | gta | tcc | gct | cgc | tca | cta | ctc | aag | agc | 687 |
| Phe | Val | Phe | Ser | Gly | Gly | Val | Val | Ser | Ala | Arg | Ser | Leu | Leu | Lys | Ser |     |
| 180 |     |     |     | 185 |     |     |     | 190 |     |     |     | 195 |     |     |     |     |
| agg | acc | aat | ggc | tct | aaa | agg | ttg | cct | ctt | gcc | aag | agg | ttg | att | gcg | 735 |
| Arg | Thr | Asn | Gly | Ser | Lys | Arg | Leu | Pro | Leu | Ala | Lys | Arg | Leu | Ile | Ala |     |
|     |     |     | 200 |     |     |     | 205 |     |     |     | 210 |     |     |     |     |     |
| tcg | acg | cga | cac | tct | att | cct | ctg | ctc | gtc | ctc | ggc | ctg | att | cgg | cta | 783 |
| Ser | Thr | Arg | His | Ser | Ile | Pro | Leu | Leu | Val | Leu | Gly | Leu | Ile | Arg | Leu |     |
|     |     |     | 215 |     |     |     | 220 |     |     |     | 225 |     |     |     |     |     |
| tac | agc | gtc | aaa | ggc | ttg | gac | tat | gcg | gag | cac | gtc | acc | gag | tac | ggc | 831 |
| Tyr | Ser | Val | Lys | Gly | Leu | Asp | Tyr | Ala | Glu | His | Val | Thr | Glu | Tyr | Gly |     |
|     |     | 230 |     |     |     | 235 |     |     |     | 240 |     |     |     |     |     |     |
| gta | cat | tgg | aac | ttc | ttc | ttt | aca | ttg | ggt | ctt | ttg | cct | ccg | ttc | gtg | 879 |
| Val | His | Trp | Asn | Phe | Phe | Phe | Thr | Leu | Gly | Leu | Leu | Pro | Pro | Phe | Val |     |
|     | 245 |     |     |     | 250 |     |     |     | 255 |     |     |     |     |     |     |     |
| gag | gtc | ttc | gac | gcc | ttg | gct | acg | atc | att | ccg | tca | tac | gag | gtt | ctc | 927 |
| Glu | Val | Phe | Asp | Ala | Leu | Ala | Thr | Ile | Ile | Pro | Ser | Tyr | Glu | Val | Leu |     |
| 260 |     |     |     | 265 |     |     |     | 270 |     |     |     | 275 |     |     |     |     |
| tcc | gtg | ggg | atc | gcc | gtc | ttg | tat | caa | gtt | gcc | cta | gag | tca | aca | gac | 975 |
| Ser | Val | Gly | Ile | Ala | Val | Leu | Tyr | Gln | Val | Ala | Leu | Glu | Ser | Thr | Asp |     |
|     |     |     | 280 |     |     |     | 285 |     |     |     | 290 |     |     |     |     |     |
| ttg | aaa | agc | tac | atc | ctc | gtc | tcc | cct | cgt | ggg | cca | agc | tta | ctg | tcc | 1023 |
| Leu | Lys | Ser | Tyr | Ile | Leu | Val | Ser | Pro | Arg | Gly | Pro | Ser | Leu | Leu | Ser |     |
|     |     |     | 295 |     |     |     | 300 |     |     |     | 305 |     |     |     |     |     |
| aag | aat | cgt | gaa | ggc | gtc | ttc | tcc | ttc | tca | ggt | tat | ctc | gcg | att | ttt | 1071 |
| Lys | Asn | Arg | Glu | Gly | Val | Phe | Ser | Phe | Ser | Gly | Tyr | Leu | Ala | Ile | Phe |     |
|     |     | 310 |     |     |     | 315 |     |     |     | 320 |     |     |     |     |     |     |
| ctt | gct | ggt | cgt | gcg | atc | ggc | att | cgg | ata | atc | cct | cgc | gga | act | tct | 1119 |
| Leu | Ala | Gly | Arg | Ala | Ile | Gly | Ile | Arg | Ile | Ile | Pro | Arg | Gly | Thr | Ser |     |
|     | 325 |     |     |     | 330 |     |     |     | 335 |     |     |     |     |     |     |     |
| ttc | tca | aga | agc | cca | gaa | cag | gcc | agg | aga | cgg | gtc | ctg | atc | agc | ctt | 1167 |
| Phe | Ser | Arg | Ser | Pro | Glu | Gln | Ala | Arg | Arg | Arg | Val | Leu | Ile | Ser | Leu |     |

-continued

```
       340                 345                 350                 355
ggc gtg caa gcg tta gtg tgg acc act ctt ttt gtg ttg aac tcc act   1215
Gly Val Gln Ala Leu Val Trp Thr Thr Leu Phe Val Leu Asn Ser Thr
            360                 365                 370 tat gcg atg gga tac gga gct aat atc cct gtc tcc cgc cgc ctc gct   1263
Tyr Ala Met Gly Tyr Gly Ala Asn Ile Pro Val Ser Arg Arg Leu Ala
        375                 380                 385 aac atg ccc tat gtc ctt tgg gtt tcg gcg ttc aac acc gcg caa ctg   1311
Asn Met Pro Tyr Val Leu Trp Val Ser Ala Phe Asn Thr Ala Gln Leu
    390                 395                 400 ttt gtg ttc tgc ctg atc gaa aca ctc tgc ttt cct gca gtt cat cgg   1359
Phe Val Phe Cys Leu Ile Glu Thr Leu Cys Phe Pro Ala Val His Arg
405                 410                 415 aca acg act caa gag agc gaa tct gag cga gtc gat ttt gct acg agc   1407
Thr Thr Thr Gln Glu Ser Glu Ser Glu Arg Val Asp Phe Ala Thr Ser
420                 425                 430                 435 cga atc atg tcg gcc ttc aat aag aac agt ctc gcg atc ttt ctt ttg   1455
Arg Ile Met Ser Ala Phe Asn Lys Asn Ser Leu Ala Ile Phe Leu Leu
            440                 445                 450 gcc aat ctt ctg act gga gct gtg aat ctg agc atc tcc aca att gat   1503
Ala Asn Leu Leu Thr Gly Ala Val Asn Leu Ser Ile Ser Thr Ile Asp
        455                 460                 465 gct aat aca gcg cag gcc atc gct gtt ctc att gga tat tca tcc att   1551
Ala Asn Thr Ala Gln Ala Ile Ala Val Leu Ile Gly Tyr Ser Ser Ile
    470                 475                 480 atc aca ggg gtt gct cta gca ttg cat cat gcc aat atc aaa gta ctt   1599
Ile Thr Gly Val Ala Leu Ala Leu His His Ala Asn Ile Lys Val Leu
485                 490                 495 cct ttc tag ggtatttacg agcaattggt ggtgtgttga agatatatag            1648
Pro Phe
500
```

```
<210> SEQ ID NO 12
<211> LENGTH: 2045
<212> TYPE: DNA
<213> ORGANISM: Cryptococcus neoformans
<220> FEATURE:
<221> NAME/KEY: CDS
<222> LOCATION: (44)..(136)
<223> OTHER INFORMATION: GWT1
<220> FEATURE:
<221> NAME/KEY: CDS
<222> LOCATION: (199)..(891)
<223> OTHER INFORMATION: GWT1
<220> FEATURE:
<221> NAME/KEY: CDS
<222> LOCATION: (943)..(1635)
<223> OTHER INFORMATION: GWT1
<220> FEATURE:
<221> NAME/KEY: CDS
<222> LOCATION: (1687)..(2004)
<223> OTHER INFORMATION: GWT1
<220> FEATURE:
<221> NAME/KEY: exon
<222> LOCATION: (44)..(136)
<220> FEATURE:
<221> NAME/KEY: intron
<222> LOCATION: (137)..(198)
<220> FEATURE:
<221> NAME/KEY: exon
<222> LOCATION: (199)..(891)
<220> FEATURE:
<221> NAME/KEY: intron
<222> LOCATION: (892)..(942)
<220> FEATURE:
<221> NAME/KEY: exon
<222> LOCATION: (943)..(1635)
<220> FEATURE:
<221> NAME/KEY: intron
```

<222> LOCATION: (1636)..(1686)
<220> FEATURE:
<221> NAME/KEY: exon
<222> LOCATION: (1687)..(2004)

<400> SEQUENCE: 12

```
gtcatagcat taaatccccg ccataataag ctactgaatt gca atg ggg gat tac      55
                                              Met Gly Asp Tyr
                                              1 aag tcg gcc aaa gag gcc ttt gtc tcg gat aac cca ggt gct tct atc     103
Lys Ser Ala Lys Glu Ala Phe Val Ser Asp Asn Pro Gly Ala Ser Ile
  5              10                  15                  20 tgg agt atc aac gct gtc agc ctg gtc gca ctg gtatgtagct cgttctccga   156
Trp Ser Ile Asn Ala Val Ser Leu Val Ala Leu
             25                  30 ggggttctgt catttggaga cgcttattaa ttgggatcgc ag gcg aca tat gct      210
                                               Ala Thr Tyr Ala
                                                            35 ctc tgg atc gcc tta tcg ccg tac atc cgt cat gga ctc ctg aac aac     258
Leu Trp Ile Ala Leu Ser Pro Tyr Ile Arg His Gly Leu Leu Asn Asn
                 40                  45                  50 tac ctg atc tgt gtt ctt ccc cta tta ttc ggg gtg acc atc ttc tca     306
Tyr Leu Ile Cys Val Leu Pro Leu Leu Phe Gly Val Thr Ile Phe Ser
             55                  60                  65 act tcg cct ctc gta ttt acc tct ttt ttg tcc att att tcc ctc gct     354
Thr Ser Pro Leu Val Phe Thr Ser Phe Leu Ser Ile Ile Ser Leu Ala
         70                  75                  80 ttc atc acg aaa tcc caa aaa tgc ttc aaa tct gtc agt tcg ccc gaa     402
Phe Ile Thr Lys Ser Gln Lys Cys Phe Lys Ser Val Ser Ser Pro Glu
     85                  90                  95 aag cca aaa ggc caa tgg cta gac gaa tca gac tcc gat gag gaa cca     450
Lys Pro Lys Gly Gln Trp Leu Asp Glu Ser Asp Ser Asp Glu Glu Pro
100                 105                 110                 115 gcg gaa cct gct tct gca gct gga tct gca gca gtc tca cca gta aag     498
Ala Glu Pro Ala Ser Ala Ala Gly Ser Ala Ala Val Ser Pro Val Lys
                120                 125                 130 ctt cta cct tcc caa gtg gcg ttc gct tcg gga tcc cta tta tct ccc     546
Leu Leu Pro Ser Gln Val Ala Phe Ala Ser Gly Ser Leu Leu Ser Pro
            135                 140                 145 gat ccg aca aca tcc ccc atg tcg cca agt agt tct tca gct tca gga     594
Asp Pro Thr Thr Ser Pro Met Ser Pro Ser Ser Ser Ser Ala Ser Gly
        150                 155                 160 cat gaa gac cct ttg ggg att atg ggc gtt aac aga cgg agg tcg cta     642
His Glu Asp Pro Leu Gly Ile Met Gly Val Asn Arg Arg Arg Ser Leu
    165                 170                 175 tta gaa gga gtt tcg ctt gat gtt ccg tca cat atc gac tcc aag gtc     690
Leu Glu Gly Val Ser Leu Asp Val Pro Ser His Ile Asp Ser Lys Val
180                 185                 190                 195 aga ata tct cct gtt ccc tac ttg agg ctc aaa aag tct agg gca acg     738
Arg Ile Ser Pro Val Pro Tyr Leu Arg Leu Lys Lys Ser Arg Ala Thr
                200                 205                 210 aag gcg caa tgg gtg aaa gaa aag gga aga tta cca ttt ttg aca gtg     786
Lys Ala Gln Trp Val Lys Glu Lys Gly Arg Leu Pro Phe Leu Thr Val
            215                 220                 225 tac cga gcg cac atg atg ctc atg act gtt atc tgc atc ttg gcg gta     834
Tyr Arg Ala His Met Met Leu Met Thr Val Ile Cys Ile Leu Ala Val
        230                 235                 240 gat ttt gaa gtg ttt cct aga tgg cag ggc aag tgc gaa gat ttt ggt     882
Asp Phe Glu Val Phe Pro Arg Trp Gln Gly Lys Cys Glu Asp Phe Gly
    245                 250                 255 act agt ctg gtaagctttc cttcagccat ggtccagtgc tcaccgctct             931
Thr Ser Leu
```

-continued

```
Thr Ser Leu
260 acttgccgta g atg gac gtg ggt gtc ggg tca ttc gtc ttt tcc ctc ggt        981
           Met Asp Val Gly Val Gly Ser Phe Val Phe Ser Leu Gly
               265                 270                 275 ctc gtc tcc aca aaa tct ctt tct cct cca cct cca act cct acg ccc        1029
Leu Val Ser Thr Lys Ser Leu Ser Pro Pro Pro Pro Thr Pro Thr Pro
                280                 285                 290 tcc tcg ccc gct ctc aac tct cac atc att ccc ctc acc ccg tcc ccg        1077
Ser Ser Pro Ala Leu Asn Ser His Ile Ile Pro Leu Thr Pro Ser Pro
            295                 300                 305 ttc act tcc atc ctc atc tcg ctc cga aaa tcc atc ccc atc ctc gtc        1125
Phe Thr Ser Ile Leu Ile Ser Leu Arg Lys Ser Ile Pro Ile Leu Val
        310                 315                 320 ctc ggc ttt ata cgg ttg att atg gtc aag gga tct gat tat cct gag        1173
Leu Gly Phe Ile Arg Leu Ile Met Val Lys Gly Ser Asp Tyr Pro Glu
    325                 330                 335 cat gtg acg gag tac ggc gtg cac tgg aat ttc ttc ttc acc ctc gca        1221
His Val Thr Glu Tyr Gly Val His Trp Asn Phe Phe Phe Thr Leu Ala
340                 345                 350                 355 ttg gtt cct gtg ctc gcc gtg ggc att cga cca ttg acg cag tgg ctt        1269
Leu Val Pro Val Leu Ala Val Gly Ile Arg Pro Leu Thr Gln Trp Leu
                360                 365                 370 cgc tgg agt gtg ctt ggg gta atc atc tct ttg ctg cat cag ctg tgg        1317
Arg Trp Ser Val Leu Gly Val Ile Ile Ser Leu Leu His Gln Leu Trp
            375                 380                 385 tta aca tat tat ctc caa tcc atc gtc ttc tca ttc ggc cgg tca ggt        1365
Leu Thr Tyr Tyr Leu Gln Ser Ile Val Phe Ser Phe Gly Arg Ser Gly
        390                 395                 400 atc ttt cta gca aac aag gaa ggc ttc tcc tct ctt cct ggt tat ctt        1413
Ile Phe Leu Ala Asn Lys Glu Gly Phe Ser Ser Leu Pro Gly Tyr Leu
    405                 410                 415 tcc ata ttt ttg atc ggc ttg tct att gga gat cat gtt tta agg ctc        1461
Ser Ile Phe Leu Ile Gly Leu Ser Ile Gly Asp His Val Leu Arg Leu
420                 425                 430                 435 agt tta cca cca aga aga gag agg gtc gtg tca gaa aca aat gaa gag        1509
Ser Leu Pro Pro Arg Arg Glu Arg Val Val Ser Glu Thr Asn Glu Glu
                440                 445                 450 cat gag cag agt cat ttt gag aga aaa aaa ttg gat ttg att atg gag        1557
His Glu Gln Ser His Phe Glu Arg Lys Lys Leu Asp Leu Ile Met Glu
            455                 460                 465 ttg att gga tat agc tta ggc tgg tgg gca ctc tta gga ggc tgg att        1605
Leu Ile Gly Tyr Ser Leu Gly Trp Trp Ala Leu Leu Gly Gly Trp Ile
        470                 475                 480 tgg gcc ggc ggg gag gta tcc agg cgt tta gtaagtggac atctttggta         1655
Trp Ala Gly Gly Glu Val Ser Arg Arg Leu
    485                 490 atattgtacc tatactaatc cctgcataaa g gcc aac gct cct tat gta ttt        1707
                                   Ala Asn Ala Pro Tyr Val Phe
                                       495                 500 tgg gta gcg gca tac aat acc acc ttt ctc ctc ggc tac ctc ctc ctt        1755
Trp Val Ala Ala Tyr Asn Thr Thr Phe Leu Leu Gly Tyr Leu Leu Leu
                505                 510                 515 acc cac att att cca tct ccc acc tct tcc caa aca tca cca tcg atc        1803
Thr His Ile Ile Pro Ser Pro Thr Ser Ser Gln Thr Ser Pro Ser Ile
            520                 525                 530 tta gtg cct ccc ttg ctc gac gct atg aat aaa aac ggt ctc gcg ata        1851
Leu Val Pro Pro Leu Leu Asp Ala Met Asn Lys Asn Gly Leu Ala Ile
        535                 540                 545 ttt ttg gcg gcc aac ttg ctt aca gga ctg gtg aat gtg agc atg aag        1899
Phe Leu Ala Ala Asn Leu Leu Thr Gly Leu Val Asn Val Ser Met Lys
```

-continued

```
                Phe Leu Ala Ala Asn Leu Leu Thr Gly Leu Val Asn Val Ser Met Lys
                            550                 555                 560 aca atg tat gcg ccg gcg tgg ttg tca atg ggg gtg tta atg ttg tat            1947
Thr Met Tyr Ala Pro Ala Trp Leu Ser Met Gly Val Leu Met Leu Tyr
565                 570                 575                 580 acc ttg aca atc agt tgt gta ggg tgg ata ctg aaa gga cgg agg atc            1995
Thr Leu Thr Ile Ser Cys Val Gly Trp Ile Leu Lys Gly Arg Arg Ile
            585                 590                 595 aag ata tag ttaaagtgtt taccatgcag gatactgagt atctcggttc a                  2045
Lys Ile <210> SEQ ID NO 13
<211> LENGTH: 1797
<212> TYPE: DNA
<213> ORGANISM: Cryptococcus neoformans
<220> FEATURE:
<221> NAME/KEY: CDS
<222> LOCATION: (1)..(1797)
<223> OTHER INFORMATION: GWT1

<400> SEQUENCE: 13 atg ggg gat tac aag tcg gcc aaa gag gcc ttt gtc tcg gat aac cca            48
Met Gly Asp Tyr Lys Ser Ala Lys Glu Ala Phe Val Ser Asp Asn Pro
1               5                   10                  15 ggt gct tct atc tgg agt atc aac gct gtc agc ctg gtc gca ctg gcg            96
Gly Ala Ser Ile Trp Ser Ile Asn Ala Val Ser Leu Val Ala Leu Ala
                20                  25                  30 aca tat gct ctc tgg atc gcc tta tcg ccg tac atc cgt cat gga ctc            144
Thr Tyr Ala Leu Trp Ile Ala Leu Ser Pro Tyr Ile Arg His Gly Leu
            35                  40                  45 ctg aac aac tac ctg atc tgt gtt ctt ccc cta tta ttc ggg gtg acc            192
Leu Asn Asn Tyr Leu Ile Cys Val Leu Pro Leu Leu Phe Gly Val Thr
        50                  55                  60 atc ttc tca act tcg cct ctc gta ttt acc tct ttt ttg tcc att att            240
Ile Phe Ser Thr Ser Pro Leu Val Phe Thr Ser Phe Leu Ser Ile Ile
65                  70                  75                  80 tcc ctc gct ttc atc acg aaa tcc caa aaa tgc ttc aaa tct gtc agt            288
Ser Leu Ala Phe Ile Thr Lys Ser Gln Lys Cys Phe Lys Ser Val Ser
                85                  90                  95 tcg ccc gaa aag cca aaa ggc caa tgg cta gac gaa tca gac tcc gat            336
Ser Pro Glu Lys Pro Lys Gly Gln Trp Leu Asp Glu Ser Asp Ser Asp
                100                 105                 110 gag gaa cca gcg gaa cct gct tct gca gct gga tcg gca gca gtc tca            384
Glu Glu Pro Ala Glu Pro Ala Ser Ala Ala Gly Ser Ala Ala Val Ser
            115                 120                 125 cca gta aag ctt cta cct tcc caa gtg gcg ttc gct tcg gga tcc cta            432
Pro Val Lys Leu Leu Pro Ser Gln Val Ala Phe Ala Ser Gly Ser Leu
        130                 135                 140 tta tct ccc gat ccg aca aca tcc ccc atg tcg cca agt agt tct tca            480
Leu Ser Pro Asp Pro Thr Thr Ser Pro Met Ser Pro Ser Ser Ser Ser
145                 150                 155                 160 gct tca gga cat gaa gac cct ttg ggg att atg ggc gtt aac aga cgg            528
Ala Ser Gly His Glu Asp Pro Leu Gly Ile Met Gly Val Asn Arg Arg
                165                 170                 175 agg tcg cta tta gaa gga gtt tcg ctt gat gtt ccg tca cat atc gac            576
Arg Ser Leu Leu Glu Gly Val Ser Leu Asp Val Pro Ser His Ile Asp
            180                 185                 190 tcc aag gtc aga ata tct cct gtt ccc tac ttg agg ctc aaa aag tct            624
Ser Lys Val Arg Ile Ser Pro Val Pro Tyr Leu Arg Leu Lys Lys Ser
        195                 200                 205 agg gca acg aag gcg caa tgg gtg aaa gaa aag gga aga tta cca ttt            672
Arg Ala Thr Lys Ala Gln Trp Val Lys Glu Lys Gly Arg Leu Pro Phe
```

```
                210                 215                 220
ttg aca gtg tac cga gcg cac atg atg ctc atg act gtt atc tgc atc        720
Leu Thr Val Tyr Arg Ala His Met Met Leu Met Thr Val Ile Cys Ile
225                 230                 235                 240 ttg gcg gta gat ttt gaa gtg ttt cct aga tgg cag ggc aag tgc gaa        768
Leu Ala Val Asp Phe Glu Val Phe Pro Arg Trp Gln Gly Lys Cys Glu
                    245                 250                 255 gat ttt ggt act agt ctg atg gac gtg ggt gtc ggg tca ttc gtc ttt        816
Asp Phe Gly Thr Ser Leu Met Asp Val Gly Val Gly Ser Phe Val Phe
                260                 265                 270 tcc ctc ggt ctc gtc tcc aca aaa tct ctt tct cct cca cct cca act        864
Ser Leu Gly Leu Val Ser Thr Lys Ser Leu Ser Pro Pro Pro Pro Thr
            275                 280                 285 cct acg ccc tcc tcg ccc gct ctc aac tct cac atc att ccc ctc acc        912
Pro Thr Pro Ser Ser Pro Ala Leu Asn Ser His Ile Ile Pro Leu Thr
        290                 295                 300 ccg tcc ccg ttc act tcc atc ctc atc tcg ctc cga aaa tcc atc ccc        960
Pro Ser Pro Phe Thr Ser Ile Leu Ile Ser Leu Arg Lys Ser Ile Pro
305                 310                 315                 320 atc ctc gtc ctc ggc ttt ata cgg ttg att atg gtc aag gga tct gat        1008
Ile Leu Val Leu Gly Phe Ile Arg Leu Ile Met Val Lys Gly Ser Asp
                    325                 330                 335 tat cct gag cat gtg acg gag tac ggc gtg cac tgg aat ttc ttc ttc        1056
Tyr Pro Glu His Val Thr Glu Tyr Gly Val His Trp Asn Phe Phe Phe
                340                 345                 350 acc ctc gca ttg gtt cct gtg ctc gcc gtg ggc att cga cca ttg acg        1104
Thr Leu Ala Leu Val Pro Val Leu Ala Val Gly Ile Arg Pro Leu Thr
            355                 360                 365 cag tgg ctt cgc tgg agt gtg ctt ggg gta atc atc tct ttg ctg cat        1152
Gln Trp Leu Arg Trp Ser Val Leu Gly Val Ile Ile Ser Leu Leu His
        370                 375                 380 cag ctg tgg tta aca tat tat ctc caa tcc atc gtc ttc tca ttc ggc        1200
Gln Leu Trp Leu Thr Tyr Tyr Leu Gln Ser Ile Val Phe Ser Phe Gly
385                 390                 395                 400 cgg tca ggt atc ttt cta gca aac aag gaa ggc ttc tcc tct ctt cct        1248
Arg Ser Gly Ile Phe Leu Ala Asn Lys Glu Gly Phe Ser Ser Leu Pro
                    405                 410                 415 ggt tat ctt tcc ata ttt ttg atc ggc ttg tct att gga gat cat gtt        1296
Gly Tyr Leu Ser Ile Phe Leu Ile Gly Leu Ser Ile Gly Asp His Val
                420                 425                 430 tta agg ctc agt tta cca cca aga aga gag agg gtc gtg tca gaa aca        1344
Leu Arg Leu Ser Leu Pro Pro Arg Arg Glu Arg Val Val Ser Glu Thr
            435                 440                 445 aat gaa gag cat gag cag agt cat ttt gag aga aaa aaa ttg gat ttg        1392
Asn Glu Glu His Glu Gln Ser His Phe Glu Arg Lys Lys Leu Asp Leu
        450                 455                 460 att atg gag ttg att gga tat agc tta ggc tgg tgg gca ctc tta gga        1440
Ile Met Glu Leu Ile Gly Tyr Ser Leu Gly Trp Trp Ala Leu Leu Gly
465                 470                 475                 480 ggc tgg att tgg gcc ggc ggg gag gta tcc agg cgt tta gcc aac gct        1488
Gly Trp Ile Trp Ala Gly Gly Glu Val Ser Arg Arg Leu Ala Asn Ala
                    485                 490                 495 cct tat gta ttt tgg gta gcg gca tac aat acc acc ttt ctc ctc ggc        1536
Pro Tyr Val Phe Trp Val Ala Ala Tyr Asn Thr Thr Phe Leu Leu Gly
                500                 505                 510 tac ctc ctc ctt acc cac att att cca tct ccc acc tct tcc caa aca        1584
Tyr Leu Leu Leu Thr His Ile Ile Pro Ser Pro Thr Ser Ser Gln Thr
            515                 520                 525 tca cca tcg atc tta gtg cct ccc ttg ctc gac gct atg aat aaa aac        1632
Ser Pro Ser Ile Leu Val Pro Pro Leu Leu Asp Ala Met Asn Lys Asn
```

```
                530                 535                 540
ggt ctc gcg ata ttt ttg gcg gcc aac ttg ctt aca gga ctg gtg aat        1680
Gly Leu Ala Ile Phe Leu Ala Ala Asn Leu Leu Thr Gly Leu Val Asn
545                 550                 555                 560 gtg agc atg aag aca atg tat gcg ccg gcg tgg ttg tca atg ggg gtg        1728
Val Ser Met Lys Thr Met Tyr Ala Pro Ala Trp Leu Ser Met Gly Val
                565                 570                 575 tta atg ttg tat acc ttg aca atc agt tgt gta ggg tgg ata ctg aaa        1776
Leu Met Leu Tyr Thr Leu Thr Ile Ser Cys Val Gly Trp Ile Leu Lys
                580                 585                 590 gga cgg agg atc aag ata tag                                            1797
Gly Arg Arg Ile Lys Ile
        595

<210> SEQ ID NO 14
<211> LENGTH: 598
<212> TYPE: PRT
<213> ORGANISM: Cryptococcus neoformans
<220> FEATURE:
<223> OTHER INFORMATION: GWT1

<400> SEQUENCE: 14

Met Gly Asp Tyr Lys Ser Ala Lys Glu Ala Phe Val Ser Asp Asn Pro
 1               5                  10                  15

Gly Ala Ser Ile Trp Ser Ile Asn Ala Val Ser Leu Val Ala Leu Ala
                20                  25                  30

Thr Tyr Ala Leu Trp Ile Ala Leu Ser Pro Tyr Ile Arg His Gly Leu
            35                  40                  45

Leu Asn Asn Tyr Leu Ile Cys Val Leu Pro Leu Leu Phe Gly Val Thr
        50                  55                  60

Ile Phe Ser Thr Ser Pro Leu Val Phe Thr Ser Phe Leu Ser Ile Ile
 65                 70                  75                  80

Ser Leu Ala Phe Ile Thr Lys Ser Gln Lys Cys Phe Lys Ser Val Ser
                85                  90                  95

Ser Pro Glu Lys Pro Lys Gly Gln Trp Leu Asp Glu Ser Asp Ser Asp
                100                 105                 110

Glu Glu Pro Ala Glu Pro Ala Ser Ala Ala Gly Ser Ala Ala Val Ser
            115                 120                 125

Pro Val Lys Leu Leu Pro Ser Gln Val Ala Phe Ala Ser Gly Ser Leu
        130                 135                 140

Leu Ser Pro Asp Pro Thr Thr Ser Pro Met Ser Pro Ser Ser Ser Ser
145                 150                 155                 160

Ala Ser Gly His Glu Asp Pro Leu Gly Ile Met Gly Val Asn Arg Arg
                165                 170                 175

Arg Ser Leu Leu Glu Gly Val Ser Leu Asp Val Pro Ser His Ile Asp
            180                 185                 190

Ser Lys Val Arg Ile Ser Pro Val Pro Tyr Leu Arg Leu Lys Lys Ser
        195                 200                 205

Arg Ala Thr Lys Ala Gln Trp Val Lys Glu Lys Gly Arg Leu Pro Phe
    210                 215                 220

Leu Thr Val Tyr Arg Ala His Met Met Leu Met Thr Val Ile Cys Ile
225                 230                 235                 240

Leu Ala Val Asp Phe Glu Val Phe Pro Arg Trp Gln Gly Lys Cys Glu
                245                 250                 255

Asp Phe Gly Thr Ser Leu Met Asp Val Gly Val Gly Ser Phe Val Phe
            260                 265                 270

Ser Leu Gly Leu Val Ser Thr Lys Ser Leu Ser Pro Pro Pro Pro Thr
```

```
                275                 280                 285
Pro Thr Pro Ser Ser Pro Ala Leu Asn Ser His Ile Ile Pro Leu Thr
            290                 295                 300
Pro Ser Pro Phe Thr Ser Ile Leu Ile Ser Leu Arg Lys Ser Ile Pro
305                 310                 315                 320
Ile Leu Val Leu Gly Phe Ile Arg Leu Ile Met Val Lys Gly Ser Asp
                325                 330                 335
Tyr Pro Glu His Val Thr Glu Tyr Gly Val His Trp Asn Phe Phe
            340                 345                 350
Thr Leu Ala Leu Val Pro Val Leu Ala Val Gly Ile Arg Pro Leu Thr
            355                 360                 365
Gln Trp Leu Arg Trp Ser Val Leu Gly Val Ile Ile Ser Leu Leu His
    370                 375                 380
Gln Leu Trp Leu Thr Tyr Tyr Leu Gln Ser Ile Val Phe Ser Phe Gly
385                 390                 395                 400
Arg Ser Gly Ile Phe Leu Ala Asn Lys Glu Gly Phe Ser Ser Leu Pro
                405                 410                 415
Gly Tyr Leu Ser Ile Phe Leu Ile Gly Leu Ser Ile Gly Asp His Val
            420                 425                 430
Leu Arg Leu Ser Leu Pro Pro Arg Arg Glu Arg Val Val Ser Glu Thr
            435                 440                 445
Asn Glu Glu His Glu Gln Ser His Phe Glu Arg Lys Lys Leu Asp Leu
    450                 455                 460
Ile Met Glu Leu Ile Gly Tyr Ser Leu Gly Trp Trp Ala Leu Leu Gly
465                 470                 475                 480
Gly Trp Ile Trp Ala Gly Gly Glu Val Ser Arg Arg Leu Ala Asn Ala
                485                 490                 495
Pro Tyr Val Phe Trp Val Ala Ala Tyr Asn Thr Thr Phe Leu Leu Gly
            500                 505                 510
Tyr Leu Leu Leu Thr His Ile Ile Pro Ser Pro Thr Ser Ser Gln Thr
            515                 520                 525
Ser Pro Ser Ile Leu Val Pro Pro Leu Leu Asp Ala Met Asn Lys Asn
    530                 535                 540
Gly Leu Ala Ile Phe Leu Ala Ala Asn Leu Leu Thr Gly Leu Val Asn
545                 550                 555                 560
Val Ser Met Lys Thr Met Tyr Ala Pro Ala Trp Leu Ser Met Gly Val
                565                 570                 575
Leu Met Leu Tyr Thr Leu Thr Ile Ser Cys Val Gly Trp Ile Leu Lys
            580                 585                 590
Gly Arg Arg Ile Lys Ile
        595

<210> SEQ ID NO 15
<211> LENGTH: 35
<212> TYPE: DNA
<213> ORGANISM: Artificial Sequence
<220> FEATURE:
<223> OTHER INFORMATION: synthetic PCR amplification primer for
      Saccharomyces cerevisiae GWT1 gene

<400> SEQUENCE: 15
ggaattcatg tcgactttaa aacagagaaa agagg                              35

<210> SEQ ID NO 16
<211> LENGTH: 39
<212> TYPE: DNA
<213> ORGANISM: Artificial Sequence
```

-continued

```
<220> FEATURE:
<223> OTHER INFORMATION: synthetic PCR amplification primer for
      Saccharomyces cerevisiae GWT1 gene

<400> SEQUENCE: 16
gcatcgattt atagcttaat gaatattctt tttctatac                              39

<210> SEQ ID NO 17
<211> LENGTH: 60
<212> TYPE: DNA
<213> ORGANISM: Artificial Sequence
<220> FEATURE:
<223> OTHER INFORMATION: synthetic PCR amplification primer for
      Schizosaccharomyces pombe his5 gene

<400> SEQUENCE: 17
atggcaacag tacatcagga gaatatgtcg actttaaaac cggatcccg tcgtttaaac        60

<210> SEQ ID NO 18
<211> LENGTH: 60
<212> TYPE: DNA
<213> ORGANISM: Artificial Sequence
<220> FEATURE:
<223> OTHER INFORMATION: synthetic PCR amplification primer for
      Schizosaccharomyces pombe his5 gene

<400> SEQUENCE: 18
ttatagctta atgaatattc tttttctata caagaaaacc gaattcgagc tcgtttaaac       60
```

METHOD OF SCREENING FOR COMPOUNDS THAT INHIBIT THE ENZYMATIC ACTIVITY OF GWT1 GENE PRODUCT

REFERENCE TO A "SEQUENCE LISTING," A TABLE, OR A COMPUTER PROGRAM LISTING APPENDIX SUBMITTED AS AN ASCII TEXT FILE

The Sequence Listing written in file 82368-44.TXT, created on Jun. 20, 2012, 81,920 bytes, machine format IBM-PC, MS-Windows operating system, is hereby incorporated by reference in its entirety for all purposes.

TECHNICAL FIELD

The present invention relates to methods of screening for antifungal agents having the activity of inhibiting glycosylphosphatidylinositol synthase (GPI synthase), which is involved in the synthesis of fungal cell walls.

BACKGROUND ART

The present inventors noticed that adhesion to host cells is important for fungi to exert their pathogenicity, and that adhesion factors involved in fungal cell adhesion are transported to the surface layers of cell walls after glycosylphosphatidylinositol (GPI) anchors on the cell membrane (Non-Patent Document 1: Hamada K et al., Mol. Gen. Genet., 258: 53-59, 1998). Accordingly, the present inventors considered that novel antifungal agents that inhibit the synthesis of fungal cell walls and also inhibit the adhesion of fungal cells to host cells could be generated by inhibiting the process of transporting proteins anchored with glycosylphosphatidylinositol (GPI-anchored proteins) to cell walls. Thus, the present inventors started study.

DISCLOSURE OF THE INVENTION

An objective of the present invention is to develop antifungal agents for preventing pathogenic fungi from exerting pathogenicity, by inhibiting the synthesis of fungal cell walls, as well as by inhibiting fungal cell adhesion to host cells, by inhibition of the transport of GPI-anchored proteins to fungal cell walls.

In WO 02/04626, the present inventors found the following proteins involved in the process of transporting GPI-anchored proteins to cell walls: the proteins of *Saccharomyces cerevisiae* encoded by DNAs comprising the nucleotide sequence of SEQ ID NO: 1; the proteins of *Candida albicans* encoded by DNAs comprising the nucleotide sequences of SEQ ID NOs: 3 and 5; the proteins of *Schizosaccharomyces pombe* encoded by DNAs comprising the nucleotide sequence of SEQ ID NO: 7; the proteins of *Aspergillus fumigatus* encoded by DNAs comprising the nucleotide sequences of SEQ ID NOs: 9 and 11; and the proteins of *Cryptococcus neoformans* encoded by DNAs comprising the nucleotide sequences of SEQ ID NOs: 12 and 13. These nucleotide sequences were called GWT1 genes. In addition, the inventors found that GWT1 gene-deficient fungi can not synthesize cell walls. Furthermore, the inventors found that the compound represented by formula (Ia) binds to the above-described proteins to inhibit the transport of GPI-anchored proteins to cell walls, thus inhibiting the synthesis of fungal cell walls.

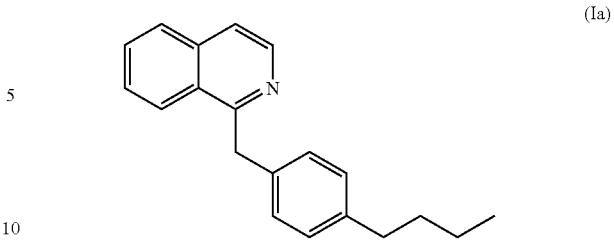

(Ia)

The inventors then found that the GWT1 gene product (hereinafter referred to as "GWT1 protein") has the activity of synthesizing glucosaminyl-acylphosphatidylinositol (GlcN-(acyl)PI) by transferring an acyl group to GlcN-PI in the GPI biosynthesis pathway (FIG. 1; Kinoshita and Inoue, Curr Opin Chem Biol 2000 December; 4(6): 632-8; Ferguson et al., Biochim Biophys Acta 1999 Oct. 8; 1455 (2-3): 327-40). The inventors conceived that compounds inhibiting the synthesis of fungal cell walls could be found by screening for compounds that inhibit this activity, and thus completed the present invention.

Specifically, the present invention provides [1] to [4] as described below.

[1] A method of screening for a compound having an antifungal activity, wherein the method comprises the steps of:

(1) contacting a test sample with an overexpressed protein encoded by the GWT1 gene;

(2) detecting GlcN-(acyl)PI; and (3) selecting the test sample that decreases GlcN-(acyl)PI.

The "GWT1" gene refers to a gene involved in the synthesis of fungal cell walls, which was disclosed in WO 02/04626. The term "overexpressed" does not refer to expression of native genes, but to the expression of exogenously introduced genes.

"GlcN-(acyl)PI" refers to glucosaminyl-acylphosphatidylinositol in which an acyl group is linked with the inositol of glucosaminyl-phosphatidylinositol (GlcN-PI) in the GPI biosynthesis pathway (FIG. 1; Kinoshita and Inoue, Curr Opin Chem Biol 2000 December; 4(6):632-8; Ferguson et al., Biochim Biophys Acta 1999 Oct. 8; 1455(2-3):327-40).

[2] The method of [1], wherein the GWT1 gene is any one of the following:

(a) a DNA encoding a protein comprising the amino acid sequence of SEQ ID NO: 2, 4, 6, 8, 10, or 14;

(b) a DNA comprising the nucleotide sequence of SEQ ID NO: 1, 3, 5, 7, 9, 11, 12, or 13;

(c) a DNA hybridizing to the DNA comprising the nucleotide sequence of SEQ ID NO: 1, 3, 5, 7, 9, 11, 12, or 13 under stringent conditions; and (d) a DNA encoding a protein comprising the amino acid sequence of SEQ ID NO: 2, 4, 6, 8, 10, or 14, wherein one or more amino acids have been added, deleted, substituted, and/or inserted.

The term "stringent conditions" means, for example, hybridization in 4×SSC at 65° C. followed by washing with 0.1×SSC at 65° C. for one hour. Alternatively, stringent conditions refer to hybridization in 4×SSC with 50% formamide at 42° C. Other acceptable conditions may be hybridization in PerfectHyb™ solution (TOYOBO) at 65° C. for 2.5 hours, followed by washing with (1) 2×SSC, 0.05% SDS at 25° C. for five minutes; (2) 2×SSC, 0.05% SDS at 25° C. for 15 minutes; and (3) 0.1×SSC, 0.1% SDS at 50° C. for 20 minutes.

The "protein comprising an amino acid sequence in which one or more amino acids have been added, deleted, substituted, and/or inserted" can be prepared by methods known to those skilled in the art, for example, by site-directed mutagenesis (Sambrook, J., Fritsch, E. F., and Maniatis, T. (1989) Molecular Cloning: A Laboratory Manual, Cold Spring Harbor Laboratory, Cold Spring Harbor, N.Y.). Such mutations can also occur naturally. There is no limitation on the number of amino acids to be mutated, as long as the resulting protein retains the activity of transferring an acyl group to GlcN-PI. The number of amino acids to be mutated is typically 30 or less, preferably ten or less, and more preferably three or less. There is no limitation on the position of the mutated amino acids, as long as the protein retains the activity described above.

The proteins and protein mutants prepared using the above-described hybridization techniques normally have high homology (for example, 60% or higher, 70% or higher, 80% or higher, 90% or higher, or 95% or higher homology) to proteins consisting of the amino acid sequence of SEQ ID NO: 2, 4, 6, 8, 10, or 14 at the amino acid level. The amino acid sequence homology can be determined using a BLASTx program (at the amino acid level; Altschul et al., J. Mol. Biol. 215:403-410, 1990). This program is based on the BLAST algorithm of Karlin and Altschul (Proc. Natl. Acad. Sci. USA 87:2264-2268, 1990; Proc. Natl. Acad. Sci. USA 90:5873-5877, 1993). When the amino acid sequences are analyzed using BLASTX, parameters of, for example, score=50 and wordlength=3 are used. Alternatively, when using the Gapped BLAST program, the amino acid sequences can be analyzed by the method described by Altschul et al. (Nucleic. Acids. Res. 25:3389-3402, 1997). When the BLAST and Gapped BLAST programs are used, the default parameter values for each program are used. Specific procedures for these analyses are known in the art (www.ncbi.nlm.nih.gov).

[3] The method of claim 1 or 2, wherein the step of detecting the acylated GPI is thin-layer chromatography.

[4] The method of any one of [1] to [3], wherein the method further comprises a step 4, of determining whether the selected test sample inhibits the process of transporting a GPI-anchored protein to a fungal cell wall, whether the test sample inhibits the expression of a GPI-anchored protein on a fungal cell surface, or whether the test sample inhibits the proliferation of a fungi.

Methods for preparing GWT1 protein [1], and methods for determining transacylation activity [2] of the present invention are disclosed below.

1. Methods for Preparing GWT1 Protein

GWT1 protein is prepared from a fungal membrane fraction, preferably that of S. cerevisiae, C. albicans, S. pombe, A. fumigatus, or C. neoformans, and more preferably S. cerevisiae. The transacylation activity may be determined by using the prepared membrane fraction directly or after purification. The transacylation activity can be readily measured by introducing a DNA of the nucleotide sequence of SEQ ID NO: 1, 3, 5, 7, 9, 11, 12, or 13 into fungal cells to overexpress the GWT1 protein. This procedure can be specifically described using S. cerevisiae, as follows:

(1) Introduction of the GWT1 Gene

The GWT1 gene can be prepared by carrying out PCR using fungal DNAs as templates, and primers designed based on a nucleotide sequence of SEQ ID NO: 1, 3, 5, 7, 9, 11, 12, or 13.

The GWT1 expression plasmid is prepared by inserting an appropriate promotor and terminator, such as a GAPDH promoter and a GAPDH terminator derived from pKT10 (Tanaka et al., Mol. Cell Biol., 10: 4303-4313, 1990), into the multi-cloning site of an expression vector that functions in S. cerevisiae, such as YEp352, and inserting the GWT1 gene into the expression vector. S. cerevisiae cells of, for example, G2-10 strain, are incubated while shaking in an appropriate medium such as yeast extract-polypeptone-dextrose (YPD) medium at an appropriate temperature, for example, at 30° C. The fungal cells are harvested at the late logarithmic growth phase. After washing, GWT1 expression plasmids are introduced into S. cerevisiae cells, for example, by the lithium acetate method. The lithium acetate method is described in the Users Manual attached to YEAST MAKER™ Yeast Transformation System (Clontech). GWT1-overexpressing strain and empty vector-introduced strain can be obtained by culturing the cells in SD(ura-) medium at 30° C. for two days.

Fungal strains to which the GWT1 gene is introduced are preferably deficient strains lacking their native GWT1 gene; S. cerevisiae GWT1 gene-deficient cells can be obtained by a method described below.

PCR amplification is carried out using a marker gene, preferably S. pombe his5 gene as a template, and primers designed to obtain PCR products which comprise 30 bp, or more preferably 40 bp or more of the GWT1 gene sequence (for example, the sequence of SEQ ID NO: 1) to be deleted. The resulting PCR products are purified, and then introduced into fungal cells. Deficient strains can be obtained by screening appropriate to the marker gene, for example, by culturing the cells in his- medium when the marker is his5.

Expression vectors and gene introduction methods for fungus other than S. cerevisiae are described in: Igarashi et al., Nature 353: 80-83, 1991, for S. pombe expression vector pcL and such, and methods for introducing the vectors; Pla J et al., Yeast, 12: 1677-1702, 1996, for C. albicans expression vector pRM10 and such, and methods for introducing these vectors; Punt P J et al., GENE, 56: 117-124, 1987, for A. fumigatus expression vector pAN7-1 and such, and methods for introducing these vectors; and Monden P et al., FEMS Microbiol. Lett., 187: 41-45, 2000, for C. neoformans expression vector pPM8 and such, and methods for introducing these vectors.

Methods for preparing deficient strains of C. albicans are described in Fonzi W A et al., Genetics 134: 717-728, 1993.

(2) Methods for Preparing the Membrane Fraction

S. cerevisiae cells to which the GWT1 gene are introduced are cultured while shaking in an appropriate medium, such as SD(ura-) liquid medium, at an appropriate temperature, for example 24° C. The fungal cells are harvested in the middle logarithmic growth phase. After being washed with TM buffer (50 mM Tris-HCl (pH 7.5) and 2 mM $MgCl_2$), the fungal cells are suspended in an adequate amount (for example, 2 ml) of TM buffer+protease inhibitor (Complete™, protease inhibitor, Roche). An adequate amount (for example, 1.5 ml) of glass beads is added to the suspension. The samples are vortexed and placed on ice, and these procedures are repeated (for example, ten cycles of vortexing for 30 seconds and placing on ice for 30 seconds) to disrupt fungal cells.

The samples are centrifuged, for example, at 1000 g for five minutes, to precipitate glass beads and fungal cells which are not disrupted. The resulting supernatant is transferred to another tube, and then centrifuged, to precipitate the membrane fraction comprising organelles (total membrane fraction), for example at 13 000 g for 20 minutes. If required, the precipitate is further suspended in 1 ml of an appropriate assay buffer, and centrifuged, for example, at 1000 g for one minute to remove those components which are not suspended. The supernatant is then centrifuged, for example, at 13 000 g for 20 minutes, and the resulting precipitate is resuspended in an appropriate assay buffer to obtain a membrane fraction.

Membrane fractions from fungal cells other than *S. cerevisiae* can be prepared by the methods as described in: Yoko-o et al., Eur. J. Biochem. 257: 630-637, 1998, for *S. pombe*; Sentandreu M et al., J. Bacteriol., 180: 282-289, 1998, for *C. albicans*; Mouyna I et al., J. Biol. Chem., 275: 14882-14889, 2000, for *A. fumigatus*; and Thompson J R et al., J. Bacteriol., 181: 444-453, 1999, for *C. neoformans*.

Alternatively, GWT1 protein can be prepared by expression in cells other than fungal cells, such as mammalian cells, insect cells, and *E. coli* cells.

When mammalian cells are used, a membrane fraction can be prepared by inserting GWT1 into, for example, an overexpression vector comprising CMV promotor; introducing the vector into mammalian cells; and then carrying out the method described in Petaja-Repo et al., J. Biol. Chem., 276: 4416-23, 2001.

When insect cells are used, a membrane fraction can be prepared by preparing GWT1-expressing insect cells (such as Sf9 cells) using a baculovirus expression kit, for example, BAC-TO-BAC Baculovirus Expression system (Invitrogen); and then using the cells to carry out the method described in Okamoto et al., J. Biol. Chem., 276: 742-751, 2001.

When *E. coli* is used, GWT1 protein can be prepared by inserting GWT1 into an *E. coli* expression vector, for example, pGEX (Amersham Biosciences); and then introducing the vector into *E. coli* cells such as BL21.

2. Methods for Determining Transacylation Activity

The transacylation reaction to GPI can be detected by the method described in Costello and Orlean, J. Biol. Chem. (1992) 267: 8599-8603, or the method described in Franzot and Doering, Biochem. J. (1999) 340: 25-32. Examples of specific methods are illustrated below, however, the experimental conditions below are preferably optimized according to the GWT1 gene products to be used, as follows:

The GWT1 gene product prepared in Section 1, above, preferably a membrane fraction comprising a GWT1 gene product, is added along with test compounds to a buffer comprising: appropriate metal ions (Mg, Mn); ATP; and Coenzyme A; and preferably inhibitors that prevent the consumption of UDP-GlcNAc in other reactions, such as nikkomycin Z as an inhibitor of chitin synthesis, and tunicamycin as an inhibitor of the synthesis of asparagine-linked sugar chain. The mixture is incubated at an appropriate temperature for an appropriate period (for example, at 24° C. for 15 minutes).

Then, a GlcN-(acyl)PI precursor (for example, UDP-GlcNAc or Acyl-Coenzyme A, and preferably UDP-[$^{14}$C] GlcNAc) labeled with an appropriate label, preferably with an isotope, is added to the mixture. The resulting mixture is further incubated for an appropriate period (for example, for one hour at 24° C.). A 1:2 mixture of chloroform:methanol is added to the mixture, and stirred to stop the reaction. Lipids are then extracted from the mixture. The extracted reaction products are dissolved in an appropriate solvent, preferably in butanol, and then subjected to HPLC, thin-layer chromatography (TLC), or such, and preferably TLC, to isolate GlcN-(acyl)PI generated in the reaction. A developing solvent for TLC can be selected appropriately, and may be, for example, CHCl$_3$/CH$_3$OH/H$_2$O (65:25:4), CHCl$_3$/CH$_3$OH/1 M NH$_4$OH (10:10:3), or CHCl$_3$/pyridine/HCOOH (35:30:7), and preferably HCl$_3$/CH$_3$OH/1 M NH$_4$OH (10:10:3). The isolated GlcN-(acyl)PI is quantified by a method that accords with the label used. When labeled with an isotope, the isolated GlcN-(acyl)PI is quantified based on its radioactivity.

When a reduced amount of GlcN-(acyl)PI is produced in the presence of a test compound, the test compound is determined to comprise the activity of inhibiting transacylation by GWT1 proteins.

A test sample found to comprise the activity of inhibiting transacylation as described above, is preferably further tested to determine whether it inhibits the process of transporting GPI-anchored proteins to fungal cell walls, whether it inhibits the expression of GPI-anchored proteins on fungal cell surfaces, or whether it inhibits fungal growth. If the test results show that the test sample inhibits the process of transporting GPI-anchored proteins to fungal cell walls, inhibits the expression of GPI-anchored proteins on fungal cell surfaces, or inhibits fungal growth, then the sample is a promising candidate for an antifungal agent.

Methods that (1) use reporter enzymes; (2) use antibodies that react to glycoproteins on the surface layers of fungal cell walls; (3) test fungal cells for adhesiveness to animal cells; or (4) observe fungal cells under a light microscope or electron microscope can be used to test whether a test sample inhibits the process of transporting GPI-anchored proteins to fungal cell walls or inhibits the expression of GPI-anchored proteins on fungal cell surfaces.

Methods (1) to (4) are enclosed in WO 02/04626, and specifically illustrated in the Examples. By using the methods of (1) to (4), preferably in combination, a test sample can be determined to inhibit the process of transporting GPI-anchored proteins to fungal cell walls or to inhibit the expression of GPI-anchored proteins on fungal cell surfaces. Further, a test sample can be determined to effect the process of transporting GPI-anchored proteins to cell walls, when the inhibition by the test sample is impaired or disappears when a protein encoded by a DNA of the present invention is overexpressed in fungal cells.

Conventional methods for measuring antifungal activity can also be used to determine whether a test sample inhibits fungal growth (National Committee for Clinical Laboratory Standards. 1992. Reference method for broth dilution antifungal susceptibility testing for yeasts. Proposed standard M27-P. National Committee for Clinical Laboratory Standards, Villanova, Pa.).

BEST MODE FOR CARRYING OUT THE INVENTION

Figure 1:
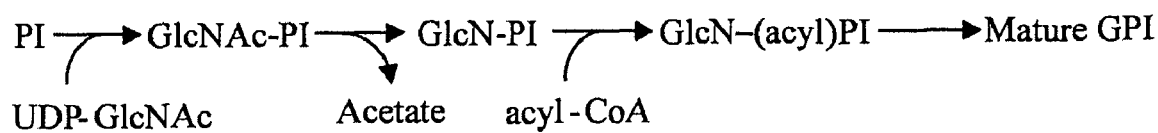
FIG. 1 shows the GPI biosynthesis pathway.

Herein below, the present invention will be specifically described using Examples, but it is not to be construed as being limited thereto.

Example 1

Preparation of Membrane Fraction Expressing GWT1 Protein (1) Preparation of GWT1 Expression Plasmid The vector for expressing in *S. cerevisiae*, YEp352GAPII vector, was prepared by inserting a GAPDH promoter and a GAPDH terminator, both derived from pKT10 (Tanaka et al., Mol. Cell Biol., 10: 4303-4313, 1990), into the multi-cloning site of YEp352; and replacing the multi-cloning site with that of pUC18. Furthermore, to facilitate the insertion of the GWT1 gene, YEp352GAPIIClaIΔSal vector was prepared by substituting the ClaI site for the SalI site in the multi-cloning site.

The *S. cerevisiae* GWT1 gene comprising the nucleotide sequence of SEQ ID NO: 1 was amplified using the primers of SEQ ID NOs: 15 and 16. The resulting PCR product was inserted into the multi-cloning site of YEp352GAPIIClaIΔSal vector to prepare the GWT1 overexpression plasmid.

(2) Preparation of *S. cerevisiae* GWT1 Gene-Deficient Strain Δgwt1

A his5 cassette comprising GWT1 sequences at both ends was amplified by PCR using the *S. pombe* his5 gene (Longtine M S et al., Yeast, 14: 953-961, 1998) as a template and the sequences of SEQ ID NOs: 17 and 18 as primers.

*S. cerevisiae* cells were cultured and harvested, and then subjected to transformation with the PCR products described above. Then, the cells were cultured in SD(His-) medium at 30° C. for five to seven days to obtain GWT1 gene-deficient strain Δgwt1.

(3) Preparation of GWT1-Expressing Cells

Cells of the Δgwt1 strain were cultured while shaking in yeast extract-polypeptone-dextrose (YPD) medium at 30° C. The cells were harvested in the late logarithmic growth phase and then washed. The expression plasmid for GWT1 was introduced to the Δgwt1 strain cells by the lithium acetate method (YEAST MAKER™ Yeast Transformation System (Clontech)). Δgwt1 strain overexpressing the GWT1 gene was obtained by culturing the cells in SD(ura-) medium at 30° C. for two days.

(4) Preparation of Membrane Fraction

Wild-type *S. cerevisiae* strain, the GWT1 gene-deficient strain Δgwt1, and the strain Δgwt1 into which the GWT1 overexpression plasmid was introduced were each cultured in 100 ml of YPD medium shaken at 24° C., and then harvested in the middle logarithmic growth phase ($OD_{600}$=1~3). The fungal cells were washed with TM buffer (50 mM Tris-HCl (pH 7.5) and 2 mM $MgCl_2$), and then suspended in 2 ml of TM buffer+protease inhibitor (1 tablet of Complete™, protease inhibitor, (Roche)/25 ml). 1.5 ml of glass beads was added to the suspension. The mixture was vortexed for 30 seconds, and then placed on ice for 30 seconds. These procedures were repeated ten times to disrupt the fungal cells. The cell homogenate was transferred into a new tube, and centrifuged at 1000 g at 4° C. for five minutes to precipitate the glass beads and undisrupted fungal cells. The supernatant was transferred to another tube, and centrifuged at 13 000g at 4° C. for 20 minutes to precipitate the membrane fraction comprising organelles (total membrane fraction). The resulting precipitate was used as the membrane fraction.

(5) Detection of Acylated GPI

In the GPI biosynthesis reaction pathway, it is known that N-acetyl-glucosaminyl-phosphatidylinositol (GlcNAc-PI) is deacetylated to generate glucosaminyl-phosphatidylinositol (GlcN-PI), to which an acyl group is then added to generate glucosaminyl-acylphosphatidylinositol (GlcN-(acyl)PI) (FIG. 1). The present inventors thus tested whether the Gwt1 protein was involved in this transacylation reaction using the method described below.

The membrane fraction preparation (300 μg protein) was diluted with a buffer consisting of 50 mM Tris-HCl (pH7.5), 2 mM $MgCl_2$, 2 mM $MnCl_2$, 1 mM ATP, 1 mM Coenzyme A, 21 μg/ml tunicamycin, 10 μM nikkomycin Z, and 0.5 mM Dithiothreitol. The solution was adjusted to a total of 140 μl for use as a reaction solution. After incubating the solution at 24° C. for 15 minutes, 15 μCi UDP-[$^{14}$C]GlcNAc was added to the tube and then incubated at 24° C. for another one hour. 1 ml of chloroform:methanol (1:2) was added to the solution and stirred to stop the reaction. Then, lipid was extracted from the solution, dried, and desalted by butanol extraction. Acylated GPI (GlcN-(acyl)PI), non-acylated GPI (GlcN-PI), and GPI which was neither acylated nor deacylated (GlcNAc-PI) were separated by thin-layer chromatography ($HCl_3$/$CH_3OH$/1 M $NH_4OH$ (10:10:3)). Each spot was detected by autoradiography.

Figure 2:
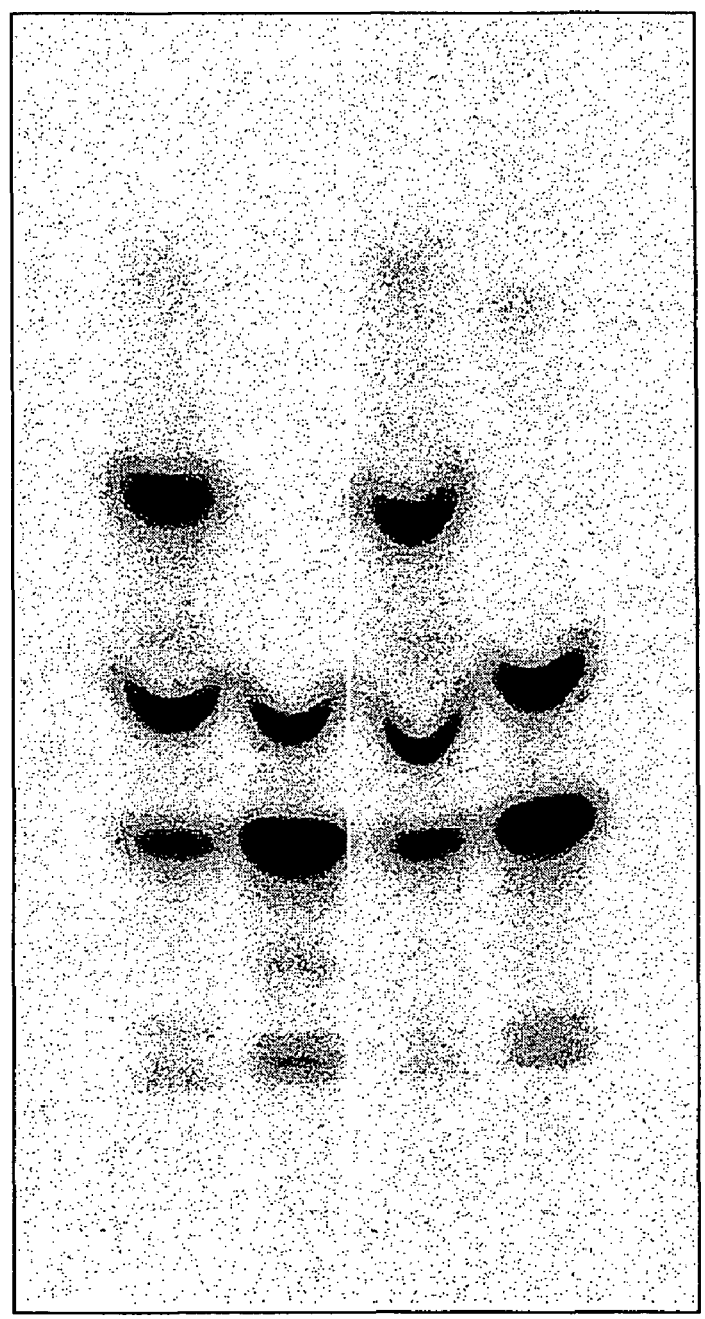
FIG. 2 is a photograph showing the results of determining GPI acylation in membrane fractions prepared from wild-type strain (WT), GWT1 gene-disrupted Δgwt1 strain (Δ), and GWT1 gene-introduced Δgwt1 strain (Δ/G).

As a result, as shown in FIG. 2, a spot for acylated GPI was not detected in the GWT1 gene-deficient strain (Δgwt1), while it was detected in the wild-type strain. The spot for acylated GPI was also detected in the GWT1 gene-introduced Δgwt1 strain, showing that this strain had recovered ability to acylate. These findings indicate that the Gwt1 protein is an enzyme that catalyzes transacylation to GPI.

The above-described results suggest that the intensity of the spot for acylated GlcN-(acyl)PI is reduced or disappears when a compound having the activity of inhibiting the activity of GWT1 gene products is present in a system for assaying GPI synthase activity. Accordingly, compounds inhibiting the enzymatic activity of a GWT1 gene product, as well as compounds inhibiting the synthesis of fungal cell walls, can be screened using the intensity of GlcN-(acyl)PI spots as an indicator.

(6) Screening for Compounds that Inhibit Acylation

The compounds below are added to the acylated GIP detection system described in (5) to measure the activity of inhibiting GPI acylation. These compounds are described in Example B2, Example B60, Example B73, and Example B85 in WO 02/04626, which discloses the GWT1 gene. In WO 02/04626, these compounds are also listed in Table 1, which shows their inhibition activity in a reporter system reflecting the activity of the GWT1 gene products. The structures of these compounds are shown below:

The compound described in Example B2: 1-(4-butylbenzyl)isoquinoline

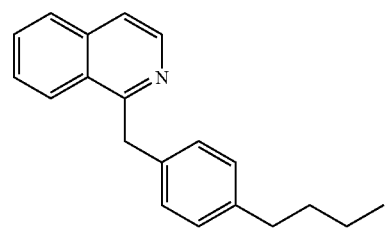

The compound described in Example B60: N-(3-(4-(1-isoquinolylmethyl)phenyl)-2-propynyl)acetamide

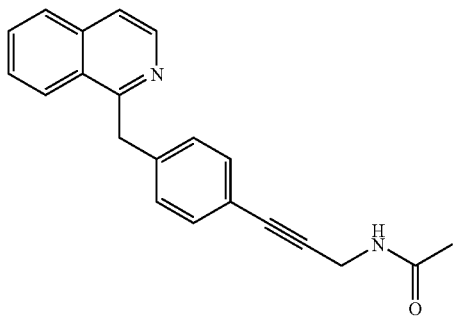

The compound described in Example B73: N-(3-(4-(1-isoquinolylmethyl)phenyl)propyl)-N-methylacetamide

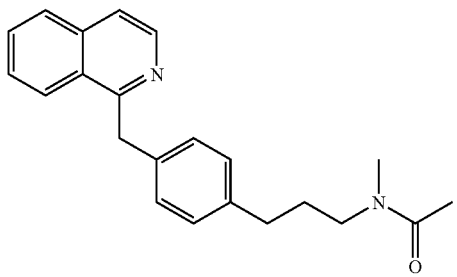

The compound in Example B85: 5-butyl-2-(1-isoquinolylmethyl)phenol

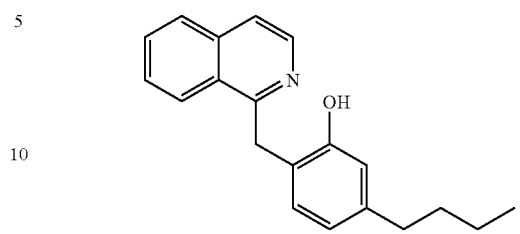

Figure 3:
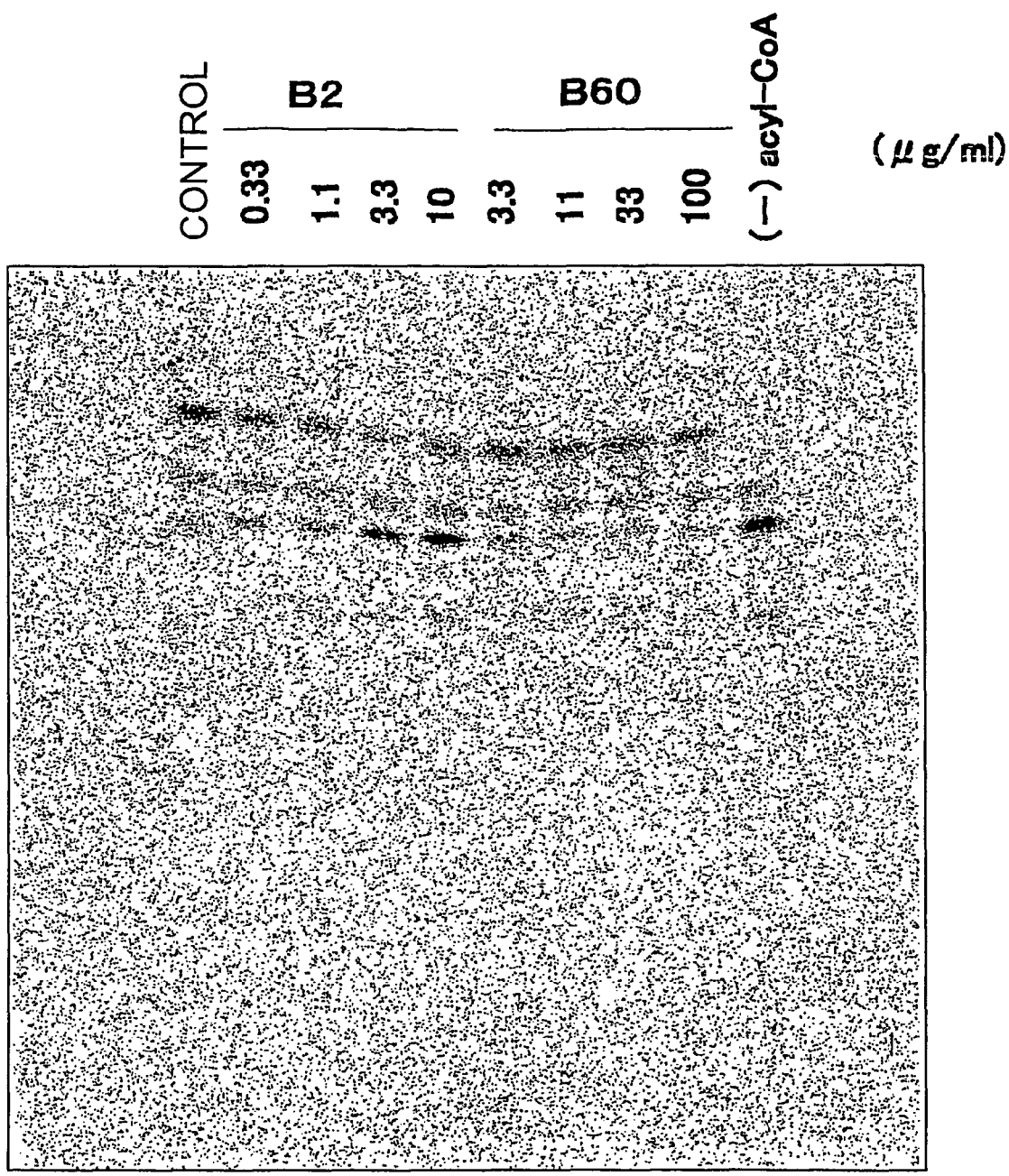
FIG. 3 is a photograph showing the results of determining the GPI acylation inhibitory activities of 1-(4-butylbenzyl) isoquinoline and N-(3-(4-(1-isoquinolylmethyl)phenyl)-2-propynyl)acetamide in the acylated GIP detection system. In WO 02/04626, which discloses the GWT1 gene, these two compounds are listed in Table 1, and described in Example B2 and Example B60 respectively.
Figure 4:
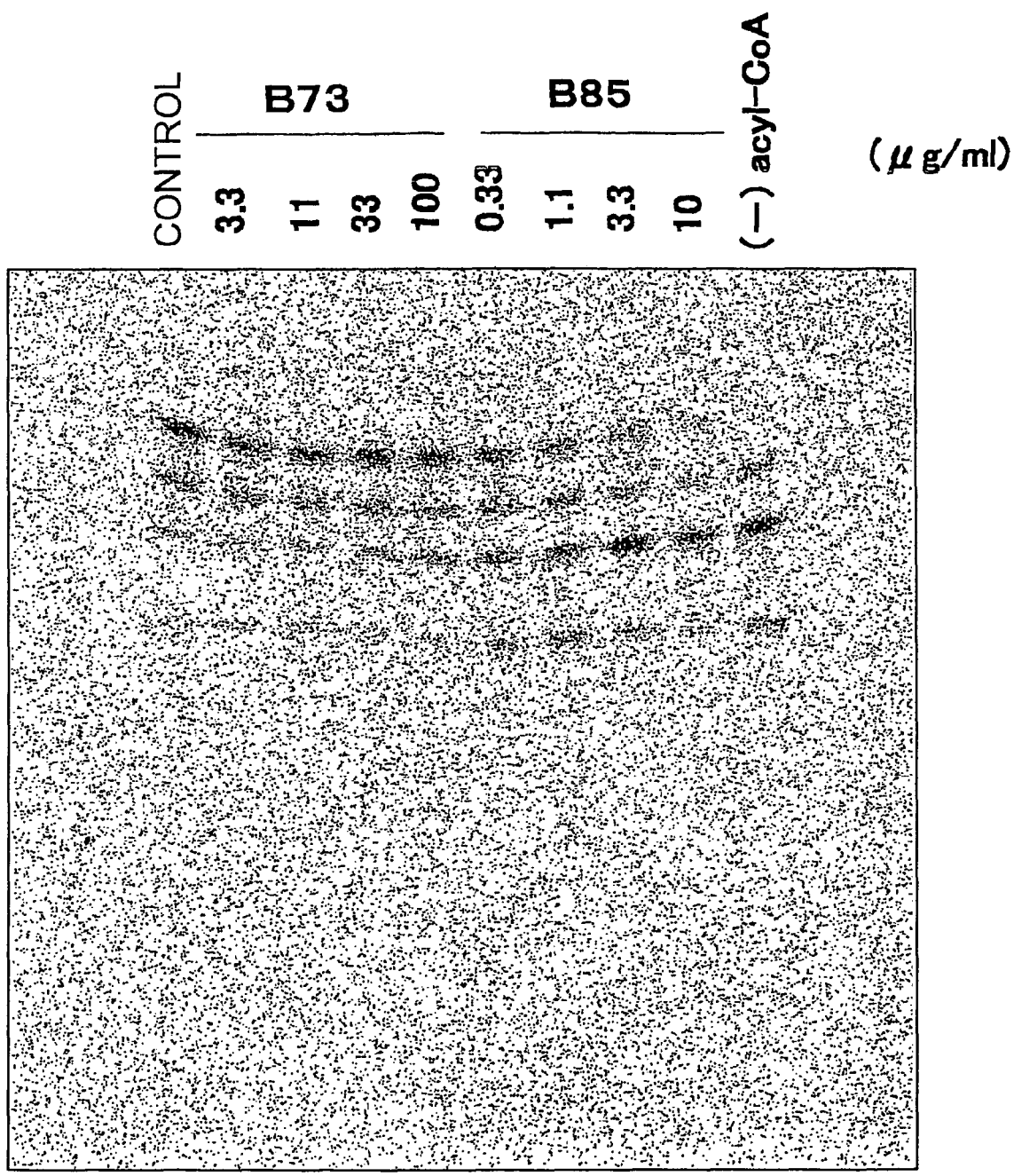
FIG. 4 is a photograph showing the results of determining the GPI acylation inhibitory activities of N-(3-(4-(1-isoquinolylmethyl)phenyl)propyl)-N-methylacetamide and 5-butyl-2-(1-isoquinolylmethyl)phenol in the acylated GIP detection system. In WO 02/04626, which discloses the GWT1 gene, these two compounds are listed in Table 1, and described in Example B73 and Example B85 respectively.

The assay results are shown in FIGS. 3 and 4. Of the compounds listed in Table 1 in WO 02/04626, the compounds described in Example B2 and Example B85, with inhibitory activities at IC50 of 1 µg/ml or less, showed a dose-dependent decrease in the spot intensity of acylated GPI. The spot intensity of the compound described in Example B73, with IC50 of 50 µg/ml, was not observed to decrease.

These results indicated that compounds inhibiting the enzymatic activity of GWT1 gene products can be screened by using the assay system for GPI acylation.

INDUSTRIAL APPLICABILITY

The present invention makes it possible to screen for compounds that inhibit the transport of GPI-anchored proteins to fungal cell walls by using a simple assay of transacylation activity.

The invention claimed is:

1. A method of screening for a sample that comprises a compound that inhibits the activity of the GWT1 protein, wherein the compound decreases GlcN-(acyl)PI, wherein the method comprises the steps of: (1) contacting a test sample with an overexpressed protein encoded by the GWT1 gene of the following (a) or (b); (a) a DNA encoding a protein comprising the amino acid sequence of SEQ ID NO:2; (b) a DNA comprising the nucleotide sequence of SEQ ID NO: 1; (2) adding glucosaminyl-acylphosphatidylinositol (GlcN-(acyl) PI) precursor to the mixture of the test sample and the protein; (3) detecting GlcN-(acyl)PI; and (4) selecting the test sample that comprises a compound that inhibits the activity of the GWT1 protein, wherein the compound decreases GlcN-(acyl)PI.

2. The method of claim 1, wherein the step of detecting the acylated glycosylphosphatidylinositol (GPI) is thin-layer chromatography.

3. The method of claim 2, wherein the method further comprises a step 4, of determining whether the selected test sample inhibits the process of transporting a glycosylphosphatidylinositol-anchored (GPI-anchored) protein to a fungal cell wall, whether the test sample inhibits the expression of a GPI-anchored protein on a fungal cell surface, or whether the test sample inhibits the proliferation of a fungi.

4. The method of claim 1, wherein the method further comprises a step 5, of determining whether the selected test sample inhibits the process of transporting a GPI-anchored protein to a fungal cell wall, whether the test sample inhibits the expression of a GPI-anchored protein on a fungal cell surface, or whether the test sample inhibits the proliferation of a fungi.

* * * * *

UNITED STATES PATENT AND TRADEMARK OFFICE
CERTIFICATE OF CORRECTION

| | |
|---|---|
| PATENT NO. | : 8,323,917 B2 |
| APPLICATION NO. | : 10/536935 |
| DATED | : December 4, 2012 |
| INVENTOR(S) | : Tsukahara et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,615 days.

Signed and Sealed this
Nineteenth Day of August, 2014

Michelle K. Lee
*Deputy Director of the United States Patent and Trademark Office*